US012589255B2

(12) United States Patent
Shamir et al.

(10) Patent No.: US 12,589,255 B2
(45) Date of Patent: Mar. 31, 2026

(54) METHODS AND APPARATUSES FOR DETECTING AND RESPONDING TO CHANGES IN A SUBJECT

(71) Applicant: Novocure GmbH, Root (CH)

(72) Inventors: Reuven Ruby Shamir, Haifa (IL); Yoram Wasserman, Haifa (IL); Zeev Bomzon, Haifa (IL); Oren Peles Zeevi, Haifa (IL); Tal Marciano, Haifa (IL)

(73) Assignee: Novocure GmbH, Baar (CH)

( * ) Notice: Subject to any disclaimer, the term of this patent is extended or adjusted under 35 U.S.C. 154(b) by 370 days.

(21) Appl. No.: 17/701,470

(22) Filed: Mar. 22, 2022

(65) Prior Publication Data

US 2022/0305277 A1      Sep. 29, 2022

Related U.S. Application Data

(60) Provisional application No. 63/196,528, filed on Jun. 3, 2021, provisional application No. 63/168,059, filed on Mar. 30, 2021, provisional application No. 63/164,957, filed on Mar. 23, 2021.

(51) Int. Cl.
      A61N 1/40            (2006.01)
(52) U.S. Cl.
      CPC ..................................... A61N 1/40 (2013.01)
(58) Field of Classification Search
      CPC ....................................................... A61N 1/40
      See application file for complete search history.

(56) References Cited

U.S. PATENT DOCUMENTS 5,304,206 A * 4/1994 Baker, Jr. ........... A61N 1/37217
                                                              607/45
5,999,848 A * 12/1999 Gord .................. A61B 5/14865
                                                              607/2

(Continued)

FOREIGN PATENT DOCUMENTS

JP          2017-522099 A      8/2017
WO          2016/014264 A1     1/2016

OTHER PUBLICATIONS

Li et al., "Evaluating the therapeutic effect of tumor treating fields (TTFields) by monitoring the impedance across TTFields electrode arrays," PeerJ, DOI 10.7717/peerj.12877, 13 pages, 2022.

*Primary Examiner* — Eric D. Bertram
(74) *Attorney, Agent, or Firm* — McCarter & English, LLP; Michael A. Sartori

(57)                ABSTRACT
A method of applying tumor treating fields to a region of interest of a subject's body corresponding to a tumor, the method including: alternately applying to the region of interest a first electric field between a first pair of locations of the subject's body and a second electric field between a second pair of locations of the subject's body; detecting a change in the region of interest of the subject's body; ceasing applying the first and second electric fields; selecting, based on the detected change, a third pair of locations of the subject's body and a fourth pair of locations of the subject's body, the third and fourth pairs of locations being different than the first and second pairs of locations; and alternately applying to the region of interest a third electric field between the third pair of locations and a fourth electric field between the fourth pair of locations.

20 Claims, 8 Drawing Sheets

(56)  References Cited

U.S. PATENT DOCUMENTS

| | | | | | |
|---|---|---|---|---|---|
| 5,999,849 | A * | 12/1999 | Gord | H02M 7/219 | 327/104 |
| 6,778,853 | B1 * | 8/2004 | Heller | A61M 37/00 | 604/20 |
| 7,214,189 | B2 * | 5/2007 | Zdeblick | A61N 1/056 | 607/34 |
| 7,340,294 | B2 * | 3/2008 | Gray | A61B 5/6843 | 600/512 |
| 7,565,205 | B2 * | 7/2009 | Palti | A61N 1/40 | 607/76 |
| 8,019,414 | B2 * | 9/2011 | Palti | A61K 41/0052 | 607/3 |
| 8,185,213 | B2 * | 5/2012 | Kveen | A61N 1/37288 | 607/125 |
| 10,441,776 | B2 * | 10/2019 | Kirson | A61K 41/0052 | |
| 10,779,875 | B2 * | 9/2020 | Palti | A61B 18/1206 | |
| 2004/0243018 | A1 * | 12/2004 | Organ | A61B 10/0041 | 600/547 |
| 2005/0209640 | A1 * | 9/2005 | Palti | A61N 1/40 | 607/2 |
| 2006/0149341 | A1 * | 7/2006 | Palti | A61N 1/0492 | 600/372 |
| 2007/0255269 | A1 * | 11/2007 | Shin | A61B 18/1206 | 606/49 |
| 2008/0188846 | A1 * | 8/2008 | Palanker | A61P 9/00 | 606/32 |
| 2009/0043346 | A1 * | 2/2009 | Palti | A61N 1/40 | 514/789 |
| 2009/0076366 | A1 * | 3/2009 | Palti | A61N 1/0492 | 600/395 |
| 2014/0148872 | A1 * | 5/2014 | Goldwasser | A61N 1/36034 | 607/45 |
| 2014/0330268 | A1 * | 11/2014 | Palti | A61P 35/00 | 606/34 |
| 2015/0088224 | A1 * | 3/2015 | Goldwasser | A61N 1/36025 | 607/45 |
| 2016/0022986 | A1 * | 1/2016 | Travers | A61N 1/0476 | |
| 2017/0014637 | A1 * | 1/2017 | Basser | A61N 1/40 | |
| 2017/0215939 | A1 * | 8/2017 | Palti | A61B 18/1206 | |
| 2017/0224990 | A1 * | 8/2017 | Goldwasser | A61N 1/0476 | |
| 2018/0050200 | A1 * | 2/2018 | Wasserman | A61B 18/14 | |
| 2018/0317848 | A1 * | 11/2018 | Gunasekar | A61B 5/6843 | |
| 2019/0117964 | A1 * | 4/2019 | Bahrami | A61N 1/327 | |
| 2020/0094051 | A1 * | 3/2020 | Park | A61N 1/36002 | |
| 2020/0155835 | A1 * | 5/2020 | Wasserman | A61N 1/0476 | |
| 2022/0096819 | A1 * | 3/2022 | Wasserman | A61N 1/0476 | |

* cited by examiner

1300

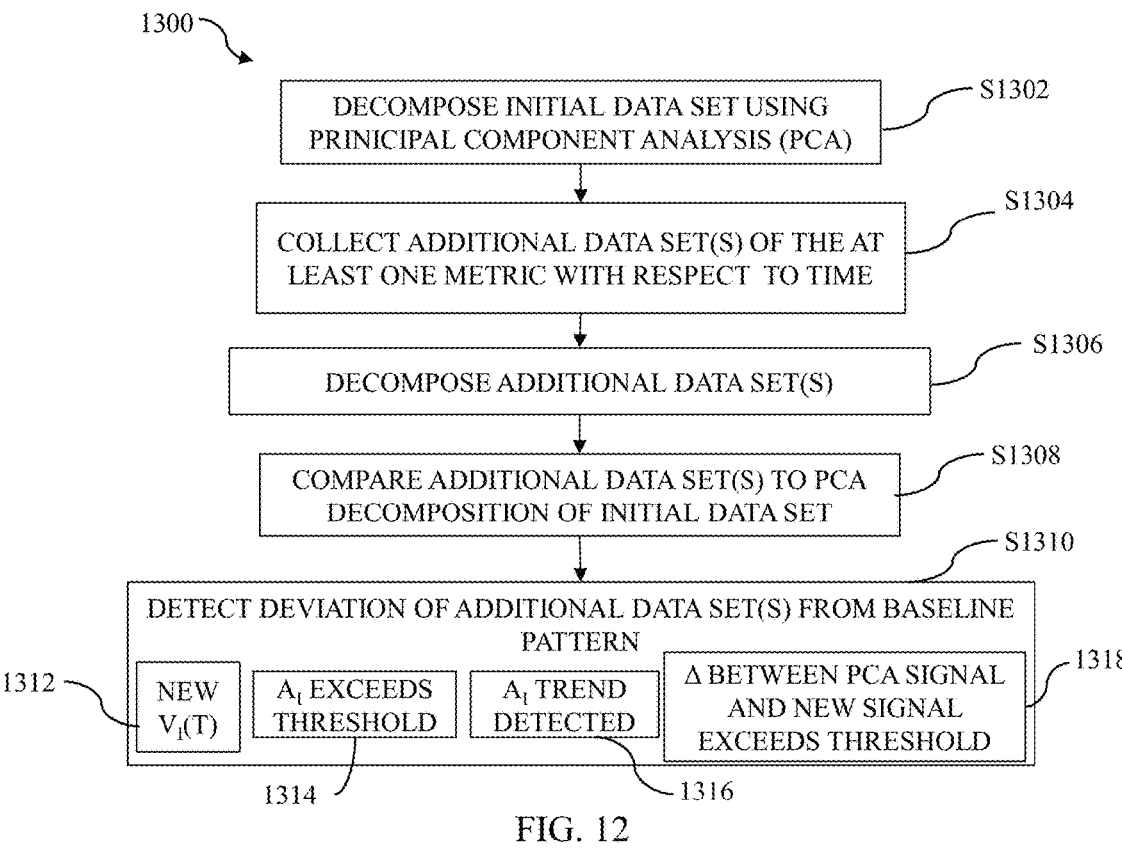

DECOMPOSE INITIAL DATA SET USING PRINICIPAL COMPONENT ANALYSIS (PCA) — S1302

COLLECT ADDITIONAL DATA SET(S) OF THE AT LEAST ONE METRIC WITH RESPECT TO TIME — S1304

DECOMPOSE ADDITIONAL DATA SET(S) — S1306

COMPARE ADDITIONAL DATA SET(S) TO PCA DECOMPOSITION OF INITIAL DATA SET — S1308

DETECT DEVIATION OF ADDITIONAL DATA SET(S) FROM BASELINE PATTERN — S1310

1312 — NEW $V_i(T)$ | $A_i$ EXCEEDS THRESHOLD | $A_i$ TREND DETECTED | Δ BETWEEN PCA SIGNAL AND NEW SIGNAL EXCEEDS THRESHOLD — 1318

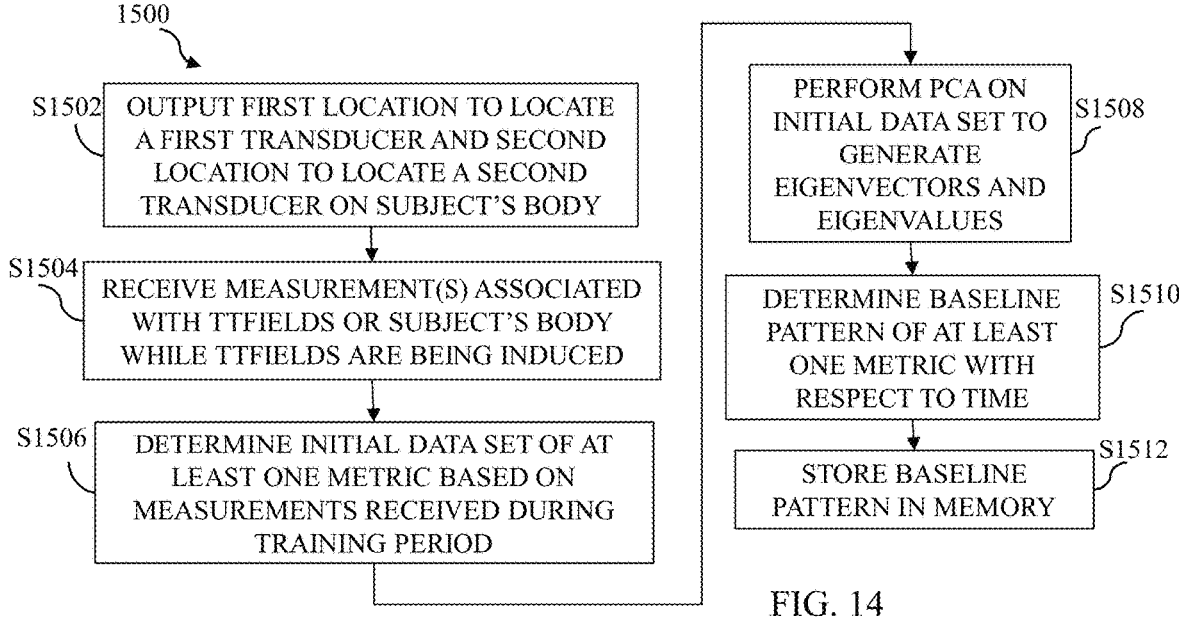

S1502 — OUTPUT FIRST LOCATION TO LOCATE A FIRST TRANSDUCER AND SECOND LOCATION TO LOCATE A SECOND TRANSDUCER ON SUBJECT'S BODY

S1504 — RECEIVE MEASUREMENT(S) ASSOCIATED WITH TTFIELDS OR SUBJECT'S BODY WHILE TTFIELDS ARE BEING INDUCED

S1506 — DETERMINE INITIAL DATA SET OF AT LEAST ONE METRIC BASED ON MEASUREMENTS RECEIVED DURING TRAINING PERIOD

PERFORM PCA ON INITIAL DATA SET TO GENERATE EIGENVECTORS AND EIGENVALUES — S1508

DETERMINE BASELINE PATTERN OF AT LEAST ONE METRIC WITH RESPECT TO TIME — S1510

STORE BASELINE PATTERN IN MEMORY — S1512

FIG. 14

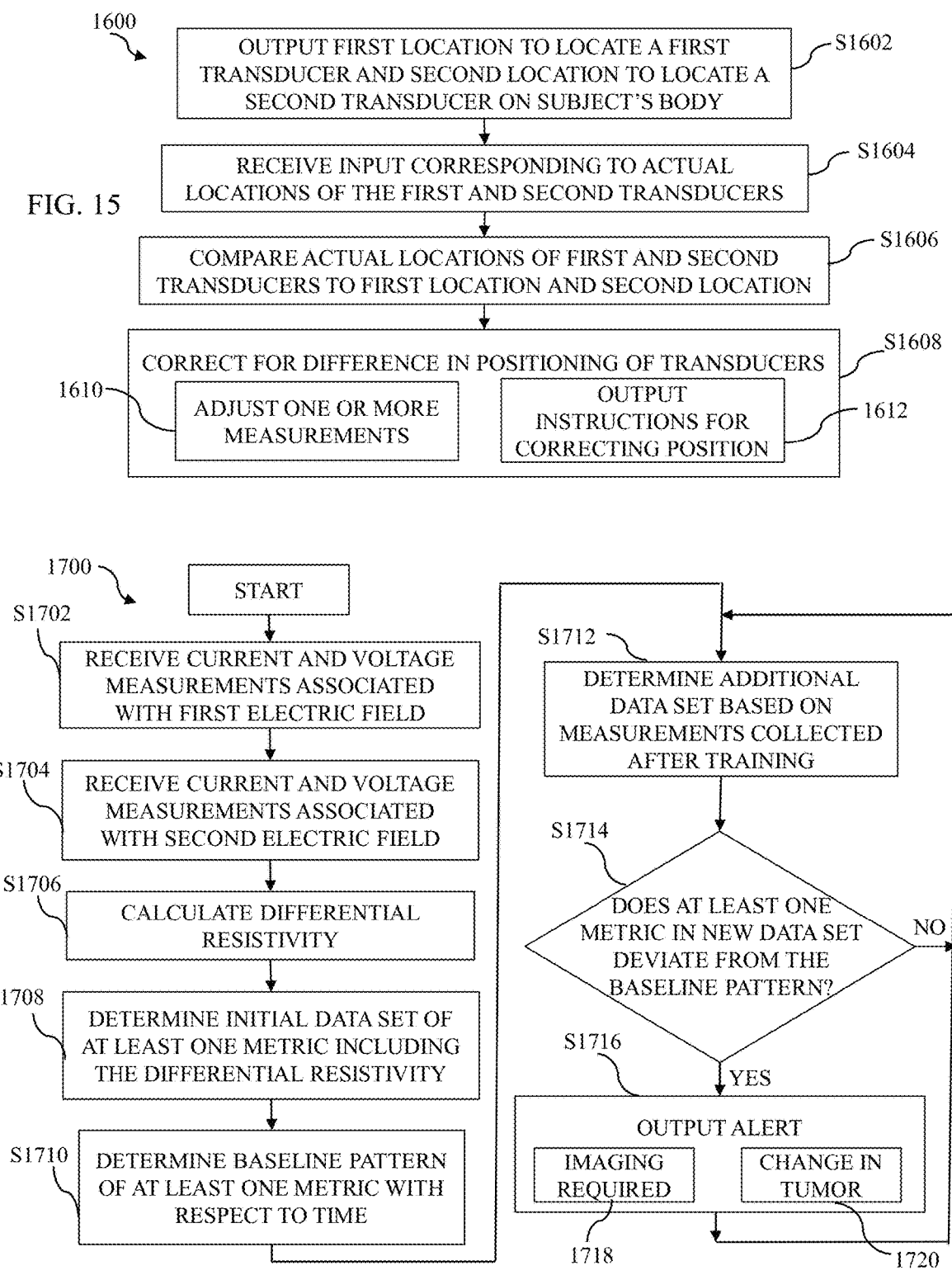

OUTPUT FIRST LOCATION TO LOCATE A FIRST TRANSDUCER AND SECOND LOCATION TO LOCATE A SECOND TRANSDUCER ON SUBJECT'S BODY — S1602

RECEIVE INPUT CORRESPONDING TO ACTUAL LOCATIONS OF THE FIRST AND SECOND TRANSDUCERS — S1604

COMPARE ACTUAL LOCATIONS OF FIRST AND SECOND TRANSDUCERS TO FIRST LOCATION AND SECOND LOCATION — S1606

CORRECT FOR DIFFERENCE IN POSITIONING OF TRANSDUCERS — S1608

1610 — ADJUST ONE OR MORE MEASUREMENTS

OUTPUT INSTRUCTIONS FOR CORRECTING POSITION — 1612

1700

START

S1702 — RECEIVE CURRENT AND VOLTAGE MEASUREMENTS ASSOCIATED WITH FIRST ELECTRIC FIELD

S1704 — RECEIVE CURRENT AND VOLTAGE MEASUREMENTS ASSOCIATED WITH SECOND ELECTRIC FIELD

S1706 — CALCULATE DIFFERENTIAL RESISTIVITY

S1708 — DETERMINE INITIAL DATA SET OF AT LEAST ONE METRIC INCLUDING THE DIFFERENTIAL RESISTIVITY

S1710 — DETERMINE BASELINE PATTERN OF AT LEAST ONE METRIC WITH RESPECT TO TIME

S1712 — DETERMINE ADDITIONAL DATA SET BASED ON MEASUREMENTS COLLECTED AFTER TRAINING

S1714 — DOES AT LEAST ONE METRIC IN NEW DATA SET DEVIATE FROM THE BASELINE PATTERN? — NO

YES

S1716 — OUTPUT ALERT

IMAGING REQUIRED

CHANGE IN TUMOR

METHODS AND APPARATUSES FOR DETECTING AND RESPONDING TO CHANGES IN A SUBJECT

CROSS-REFERENCE TO RELATED APPLICATIONS

This application claims priority to U.S. Patent Application No. 63/164,957 filed Mar. 23, 2021, U.S. Patent Application No. 63/168,059 filed Mar. 30, 2021, and U.S. Patent Application No. 63/196,528 filed Jun. 3, 2021, which are incorporated herein by reference.

BACKGROUND

Tumor treating fields (TTFields) are low intensity alternating electric fields within the intermediate frequency range, which may be used to treat tumors as described in U.S. Pat. No. 7,565,205. TTFields are induced non-invasively into the region of interest by applying AC voltages between transducers placed on the patient's body. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied between the second pair of transducers for a second interval of time to generate an electric field with field lines generally running in the right-left direction, and the system repeats this sequence.

SUMMARY OF THE INVENTION

One aspect of the invention is directed to a method of applying tumor treating fields to a region of interest of a subject's body corresponding to a tumor of the subject's body, the method including: alternately applying to the region of interest a first electric field between a first pair of locations of the subject's body and a second electric field between a second pair of locations of the subject's body; detecting a change in the region of interest of the subject's body; ceasing applying the first electric field and the second electric field; selecting, based on the detected change in the region of interest, a third pair of locations of the subject's body and a fourth pair of locations of the subject's body, the third and fourth pairs of locations being different than the first and second pairs of locations; and alternately applying to the region of interest a third electric field between the third pair of locations of the subject's body and a fourth electric field between the fourth pair of locations of the subject's body.

The above aspect of the invention is exemplary, and other aspects and variations of the invention will be apparent from the following detailed description of embodiments.

BRIEF DESCRIPTION OF THE DRAWINGS

FIGS. 5A-6B depict examples of pairs of transducers on a subject's body.

FIGS. 7 and 8 depict examples of the structure/configuration of various transducers.

FIG. 12 depicts an example of detecting a deviation of a monitored physiological metric from a baseline pattern.

FIG. 14 depicts an example of calibrating a system for detecting changes.

FIG. 15 depicts an example of correcting for a difference in transducer positioning.

FIG. 16 depicts another example of detecting a change in a subject's body.

DESCRIPTION OF EMBODIMENTS

To provide a subject with an effective TTFields treatment, precise locations at which to place transducers on the subject's body must be generated based on, for example, type, size, and/or location of the cancer in the subject's body. Determining the locations often relies on time- and resource-intensive computer simulations. In addition, existing methods fail to account for changes in the region of interest that occur during real-time treatment (e.g., due to changes in the subject's posture, physiological changes, etc.). Another difficulty is how to differentiate between physiological changes indicating a change in the region of interest and normal changes in the subject's body that occur cyclically over time. Further, there is a need to detect changes in the region of interest quickly so that TTFields treatment can be updated as soon as possible.

The inventor recognized these problems and discovered an approach to track changes in a region of interest of a subject's body during TTFields treatment and to trigger an event (e.g., new MRI; changing locations of transducers, etc.) based on the changes in the region of interest of the subject's body during TTFields treatment. By accounting for the changes in the region of interest of the subject's body in real-time treatment, the accuracy of the locations at which to place the transducers may be improved, thus improving the efficiency of TTFields treatment.

Figures 1, 2:
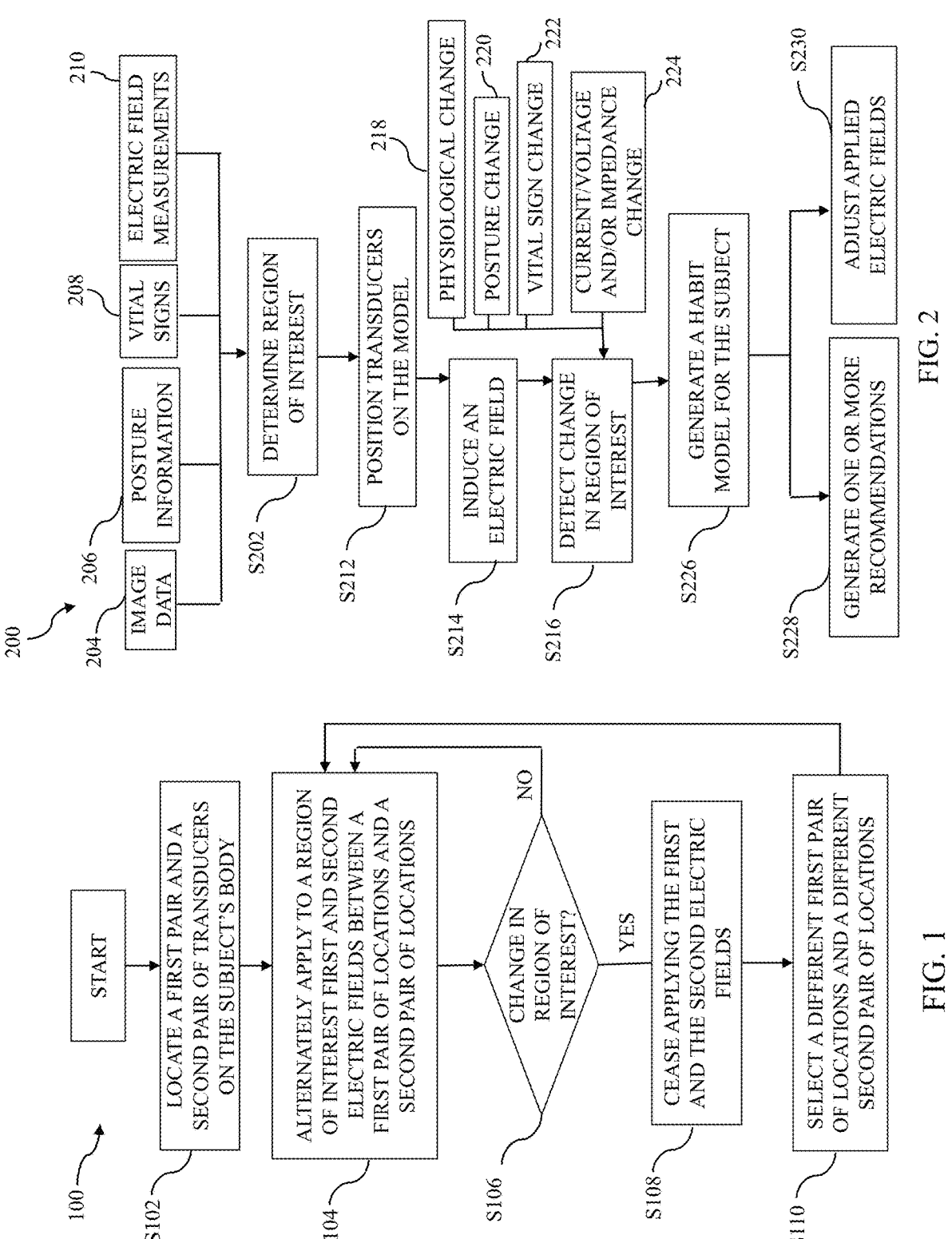
FIG. 1 depicts an example of determining the locations of transducers on a subject's body based on a change in a region of interest of the subject's body.
FIG. 2 depicts an example of determining a change in a region of interest and locations of transducers on a subject's body for applying TTFields.

FIG. 1 is a flowchart depicting an example method 100 for applying TTFields to a region of interest of a subject's body corresponding to a tumor of the subject's body. At step S102, the method 100 includes locating a first pair of transducers and a second pair of transducers on the subject's body (e.g., the first and second pairs of transducers may be located on a first and second pair of locations of the subject's body, respectively).

At step S104, the method 100 includes alternately applying, to the region of interest (e.g., tumor) of the subject's body, a first tumor treating electric field (TTField) between the first pair of locations and a second TTField between the second pair of locations. The first TTField may be produced by applying a first AC voltage generated between the first pair of locations for a time period, generation of the first TTField is ceased, and then the second TTField is produced by applying a second AC voltage between the second pair of locations for a time period.

At step S106, the method 100 includes detecting a change in the region of interest of the subject's body. The change in the region of interest may include at least one of a change in the location or a change in volume of the region of interest. Examples of determining a change in region of interest are illustrated in step S216 in FIG. 2 discussed below. Detecting the change in the region of interest may include monitoring at least one metric with respect to time and comparing the monitored metric to a baseline pattern of the at least one metric with respect to time established for the subject. A change is detected upon detecting a deviation of the monitored at least one metric from the baseline pattern. Establishing the baseline pattern, monitoring the metric(s), and comparing the metric(s) to the baseline pattern are illustrated in FIGS. 11-16.

If a change in the region of interest is not detected, the method 100 proceeds to step S104. If a change in the region of interest is detected, the method 100 proceeds to step S108, which includes ceasing applying TTFields between the first and second pairs of locations.

At step S110, the method 100 comprises selecting a third pair of locations and a fourth pair of locations based on the change in the region of interest determined at step S106. The third and fourth pairs of locations are different than the first and second pairs of locations. Then, the method 100 may proceed back to step S104 but this time alternately applying, to the region of interest, a third electric field between the third pair of locations of the subject's body and a fourth electric field between the fourth pair of locations of the subject's body. The method 100 may continually repeat with each detected change and selected change of locations.

The first pair of locations and the second pair of locations of the method 100 may correspond to locations of a first part of the first pair of transducers and a first part of the second pair of transducers, and the first TTField may be applied between the first part of the first pair of transducers and the second electric field between the first part of the second pair of transducers. In another example, the first pair of locations and the second pair of locations of the method 100 may correspond to locations of the entire transducers in each transducer pair.

Selecting the third and fourth pairs of locations at step S110 may involve selecting a second part of the first pair of transducers and a second part of the second pair of transducers based on the change in the region of interest determined at step S106, such that the third electric field is applied between the second part of the first pair of transducers and the fourth electric field is applied between the second part of the second pair of transducers. In one example, the first part of the two pairs of transducers do not overlap with one another, and the second part of the two pairs of transducers do not overlap with one another. In another example, the first part of the two pairs of transducers at least partially overlap with one another, and the second part of the two pairs of transducers at least partially overlap with one another.

Selecting the third and fourth pairs of locations at step S110 may involve re-locating the first and second pairs of transducers to the third and fourth pairs of locations, respectively, so that the third and fourth electric fields are applied between the first pair of transducers located at the third pair of locations and between the second pair of transducers located at the fourth pair of locations. In another embodiment, selecting the third and fourth pairs of locations at step S110 may involve locating a third pair of transducers at the third pair of locations and a fourth pair of transducers at the fourth pair of locations, so that the third and fourth electric fields are applied between the third pair of transducers located at the third pair of locations and between the fourth pair of transducers located at the fourth pair of locations.

FIG. 2 is a flowchart depicting an example method 200 for determining a region of interest and locations of transducers on a subject's body for applying TTFields. At step S202, the method 200 includes determining a region of interest of the subject's body corresponding to the tumor (e.g., corresponding to a location and/or volume of the tumor).

The region of interest in the subject's body may be determined by image data 204 (e.g., via computer simulations built from the image data 204). The image data 204 may include one or more images (e.g., X-ray images, magnetic resonance imaging (MRI), computerized tomography (CT) images, ultrasound images, etc.) of a portion of the subject's body.

Determining the region of interest may incorporate posture information 206 of the subject's body. Posture information 206 may be detected and/or collected by one or more sensors (e.g., accelerometers, gyroscopes, and/or magnetometers), or determined by user input. Sensor(s) may be located external to the first pair of transducers and the second pair of transducers, or may be part of at least one of the first pair of transducers or the second pair of transducers.

Determining the region of interest may be based on vital signs 208 of the subject's body. The vital signs 108 may include respiratory signs (e.g., respiratory rate, respiratory volume). Other vital signs may include body temperature, blood pressure, pulse rate, etc.

Determining the region of interest may be based on electric field measurements 210. The electric field measurements 210 may include a voltage measurement and a current measurement generated and/or collected for the TTFields applied for a desirable time period prior to a real-time TTFields treatment, and/or during a real-time TTFields treatment.

Determining the region of interest may be based on any combination of two or more factors of the image data 204, posture information 206, vital signs 208, and electric field measurements 210. As an example, the determination of the region of interest may be based on image data 204 and posture information 206. In one example, a plurality of regions of interest corresponding to a plurality of postures of the subject are determined. The plurality of regions of interest corresponding to the plurality of postures may be determined prior to real-time TTFields treatment, or may be determined and/or updated during real-time TTFields treatment.

At step S212, a first transducer is positioned at a first location and a second transducer is positioned at a second location. The locations may be selected based on the determined region of interest at step S202 to yield maximum electric field power delivered to the determined region of interest. At step S214, the method 200 comprises inducing a TTField between the first and second transducers located at the first and second locations. At step S216, the method 200 comprises detecting a change in the region of interest.

The change in the region of interest may be caused by physiological changes 218 of the subject's body. Physiological changes may include at least one of a change in tumor size, change in tumor location, weight gain, weight loss, swelling of the body, swelling in a portion of the body, or inflammation, and may be determined by image data and/or other measurements.

The change in the region of interest may be caused by a posture change 220. The posture change 220 may include a change from one of a plurality of postures to another of the plurality of postures. The plurality of postures may include at least two of standing, sitting, lying down, or one or more postures in-between standing, sitting, and lying down. In a more specific example, the lying down posture may include the subject lying on at least one of the subject's back, left side, right side, or chest. Posture changes 220 may be detected and/collected by one or more sensors, or may be entered by user input.

The change in the region of interest may be caused by a change in vital signs 222 of the subject's body. The vital sign change 222 may include a change in respiratory signs (e.g., at least one of respiratory rate or respiratory volume) of the subject, as respiratory rate and respiratory volume may change the internal volume of the torso and lead to a change in the region of interest. Other vital signs may include, for example, body temperature, blood pressure, and pulse rate. Vital sign changes 222 may be detected by sensors, or entered by user input.

In certain embodiments, the change in the region of interest may be determined based on a detected change in one or more of the factors 218-222 listed above. Additionally, or alternatively, the change in the region of interest may be determined based on a change (224) in the voltage and/or current of TTFields applied to the region of interest, a resistivity of the subject's body, and/or an impedance of the subject's body. Current measurements are indicative of a current of the TTFields passing through the subject's body between a pair of transducers, as measured at one or more electrodes in the pair of transducers. Voltage measurements are indicative of a voltage applied to the selected pair of transducers to induce the TTFields. A resistivity of the subject's body along a path of the TTField may be calculated based on the voltage and current measurements as discussed below. Further, the voltage and current measurements and/or calculated resistivity may be used to calculate an impedance of the subject's body. The resistivity calculated for one channel (e.g., between a pair of transducers) may be divided by the distance between the pair of transducers to determine an impedance of the subject's body between the pair of transducers. This calculation may be repeated for both channels used to apply alternating TTFields to the region of interest.

At step S226, the method 200 includes optionally generating a habit model for the subject based on the data collected at steps S202 and S216. The posture information 206, vital signs 208, posture change 220, vital sign change 222, and current/voltage change 224 may be collected and recorded over time during the TTFields treatment and stored with a time stamp. A habit model for the subject may be generated by a machine based on the collected and stored data, with or without additional user input. The habit model may include information regarding time stamp, posture information, and region of interest and may be presented at an output device.

As an example, a habit model may include the following exemplary information:

12:00 am-8:00 am/lying on the back/region of interest 1;
8:00-10:00 am/standing/region of interest 2;
10:00 am-2:00 pm/sitting/region of interest 3;
2:00-3:00 pm/standing and walking/region of interest 4;
3:00-8:00 pm/posture in-between sitting and lying on the back/region of interest 5;
8:00 pm-12:00 am/lying on the back/region of interest 1.

At step S228, the method 200 may include generating one or more recommendations based on the change in the region of interest obtained at step S216 and/or the habit model generated at step S226. This is similar to step S310 in FIG. 3. The recommendations may be for locations on the subject's body at which to place transducers and/or recommended parts of the transducers for applying TTFields. Recommendations may be incorporated in the habit model.

At step S230, the method 200 may include adjusting the applied electric field based on the change in the region of interest detected in step S216 and/or the habit model generated at step S226. The adjustment of the electric fields may include adjusting the location of the transducers and/or adjusting the voltage of the TTFields applied to the subject's body. The adjustments may be automatic. As an example, the method 200 may change from part 1 to part 2 of the transducers for applying the electric field at a time when the subject changes posture according to the habit model. In another example, inquiries for confirmation may be presented to the subject on a user device to confirm the change of postures before the TTFields are adjusted.

Figures 3, 4:
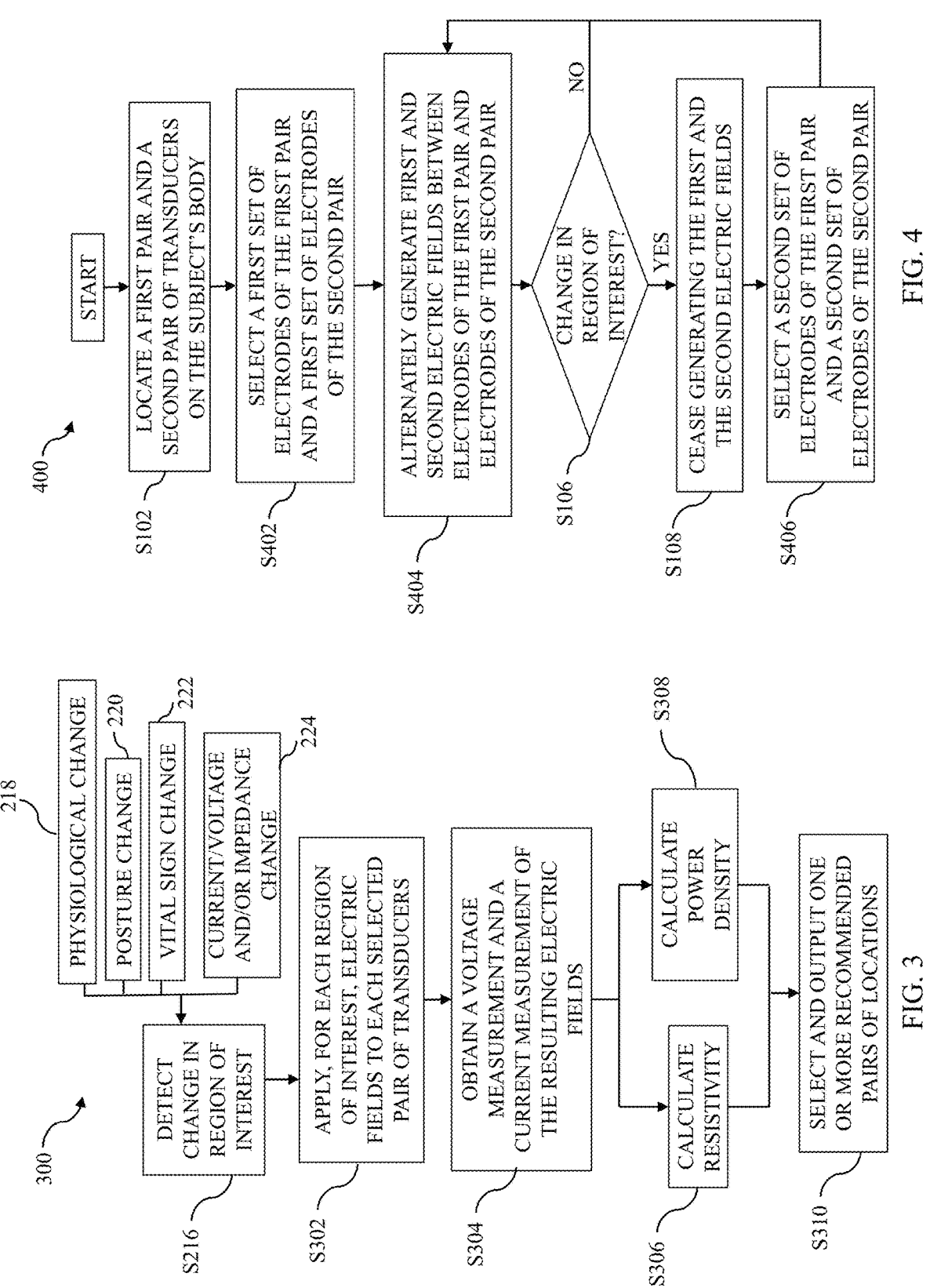
FIGS. 3 and 4 depict other examples of determining locations of transducers on a subject's body based on a change in a region of interest of the subject's body.

FIG. 3 is a flowchart depicting another example method 300 for determining locations of transducers on a subject's body for applying TTFields. The method 300 includes performing step S216 of FIG. 2. At step S302, the method 300 includes generating a plurality of regions of interest based on the obtained changes in the region of interest in step S216. This may involve determining a plurality of postures of the subject's body. The step S302 may further comprise selecting a pair of transducers for each region of interest (e.g., for each posture) and applying TTFields to each selected pair of transducers.

At step S304, for each region of interest (e.g., for each posture), the method 300 includes receiving a voltage measurement and a current measurement associated with the TTFields induced between the first and the second transducers of the selected pair of transducers. Step S304 may be a computer-implemented step in which current and voltage measurements that were obtained and/or recorded are received at a processing component of a computer.

The current and voltage measurements may be generated and/or collected (e.g., received or accessed from a log file) prior to a real-time treatment of TTFields, or in real-time or near real-time during a treatment period in which TTFields are applied. Such voltage and current measurements may be obtained at regular intervals throughout TTFields treatment.

At step S306, for each region of interest, the method 300 includes calculating a resistivity of the subject's body along a path of the TTField between the first transducer and the second transducer based on the received current and voltage measurements. The resistivity of the subject's body along the path of the TTField may be calculated by the following equation:

$$\rho = E/J \qquad \text{Equation 1}$$

Where $\rho$ is the resistivity of the subject's body along the path of the applied TTField in ohm meters ($\Omega$m); E is the magnitude of the electric field of the applied TTField in volts per meter (V/m); and J is the magnitude of the current density of the applied TTField in amperes per square meter ($A/m^2$).

The calculated resistivity may change over time in which TTFields are applied to the subject's body. Resistivity changes may be the result of, e.g., physiological changes 218, posture changes 220, vital sign changes 222, or changes in placement/attachment of transducers.

At step S308, the method 300 includes calculating a power density of the TTFields between the first transducer and the second transducer based on the received current and voltage measurements. The power density of the TTFields may be used to represent the TTFields dose delivered to the corresponding region of interest. The power density of the applied TTFields may be calculated by the following equation:

$$P=\tfrac{1}{2}\sigma E^2 \qquad\qquad \text{Equation 2}$$

Where P is the power density of the applied TTFields; σ is the conductivity of tissue; and E is the magnitude of the electric field of the applied TTFields.

The conductivity of the tissue σ may satisfy the following equation:

$$\sigma=1/\rho \qquad\qquad \text{Equation 3}$$

Therefore, the power density P may be calculated by Equations 1-3 based on voltage and current measurements of the applied TTFields.

At step S310, the method 300 includes selecting and outputting one or more recommended pairs of transducers based on the calculated resistivity and/or the calculated power density. In one example, the selection one or more recommended pairs of transducers is based on the calculated resistivity for each region of interest at step S306. Step S310 may include comparing the calculated resistivities for the plurality of pairs of transducers for each region of interest and, for each region of interest, ranking the plurality of pairs of transducers based on the calculated resistivities. The recommended transducer pairs may be selected based on the ranking. Step S310 may include, for each region of interest, selecting a first pair of transducers based on the ranking of the plurality pairs of transducers, and, for each region of interest, selecting a second pair of transducers from the remaining one or more pairs of transducers based on the ranking. In another example, the selection of the second pair of transducers is based on the selection of the first pair of transducers (e.g., based on an intersection angle with regards to the selected first pair of transducers). The second pair of transducers may be selected such that a first angle between a first line defined by the first part of the first pair of transducers and a second line defined by the first part of the second pair of transducers is approximately 90 degrees+/−20 degrees; and a second angle between a third line defined by the second part of the first pair of transducers and a fourth line defined by the second part of the second pair of transducers is approximately 90 degrees+/−20 degrees.

Step S310 may include calculating a local minimum power density (LMiPD) for a combination of two pairs of transducers in the plurality pairs of transducers and selecting the layout with a maximum LMiPD. LMiPD represents the lower of two power densities delivered by the TTFields to the region of interest via two pairs of transducers, calculated via Equation.

FIG. 4 is a flowchart depicting another example method 400 for determining the locations of transducers on a subject's body. With reference to FIG. 4, method 400 includes performing steps S102, S106, and S108 of FIG. 1. At step S402, the method 400 includes selecting a first set of electrodes of the first pair of transducers and a first set of electrodes of the second pair of transducers. Each transducer may include an array of electrode elements. The electrodes may be individually addressable electrodes, as discussed further below. The selection of these sets of electrodes may be based on the region of interest of the subject's body. At step S404, the method 400 includes alternately applying to the region of interest a first TTField between a first set of electrodes of the first pair of transducers and a second TTField between a first set of electrodes of the second pair of transducers. This is similar to step S104 in FIG. 1.

At step S406, the method 400 includes selecting a second set of electrodes of the first pair of transducers and a second set of electrodes of the second pair of transducers based on the change in region of interest determined at step S106. The selection of the second sets of electrodes of the first pair and second pair of transducers is based on the change in region of interest. A third TTField and a fourth TTField may then be alternately applied to the region of interest between the second set of electrodes of the first pair of transducers and between the second set of electrodes of the second pair of transducers. The first set of electrodes and the second set of electrodes of the first pair of transducers may not overlap with one another, or the first set of electrodes and the second set of electrodes of the first pair of transducers may partially overlap with one another. For example, there may be at least one electrode, e.g., a first electrode, that is in both the first and the second sets of electrodes of the first pair of transducers.

At least one electrode of the first pair of transducers may emit different amounts of non-zero energy during the first and third electric fields, and at least one electrode of the second pair of transducers may emit different amounts of non-zero energy during the second and fourth electric fields. In one example, the at least one electrode in both the first set and the second set of electrodes (e.g., a first electrode) emits energy during the first electric field and during the third electric field. The energy emitted by the first electrode during the first electric field may be different than the energy emitted by the first electrode during the third electric field. As a more specific example, the energy emitted by the first electrode during the first electric field may be a percentage of the energy emitted by the first electrode during the third electric field, the percentage being greater than 0% and less than 100%, or the energy emitted by the first electrode during the third electric field may be a percentage of the energy emitted by the first electrode during the first electric field, the percentage being greater than 0% and less than 100%. In another example, the first electrode emits energy during a first portion in a period of the first electric field and during a first portion in a period of the third electric field. The energy emitted during the first portion in the period of the first electric field may be different than the energy emitted during the first portion in the period of the third electric field.

In an example, the different energy emitted by the first electrode during the first electric field and the third electric field is due to the voltage signal applied to the first electrode being different during the first and third electric field. For example, the first electrode receives different voltage signals for the first and third electric fields. The first electrode may receive a first non-zero voltage during the first electric field and a second non-zero voltage during the third electric field, the first non-zero voltage different from the second non-zero voltage. In another example, the first electrode receives a same amplitude of voltage during the first and third electric fields but during different time segments of periods of the first and third electric fields.

In another example, the different energy emitted by the first electrode during the first electric field and the third electric field is due to a capacitance change of the first electrode. For example, the first electrode has a first capacitance during the first electric field and has a second capacitance during the third electric field. In this example, the first electrode may receive the same voltage signal during the first and third electric fields. Examples of structures in which different energy may be emitted by a first electrode are discussed below with reference to FIG. 8.

Figures 5A, 5B, 6A, 6B, 7:
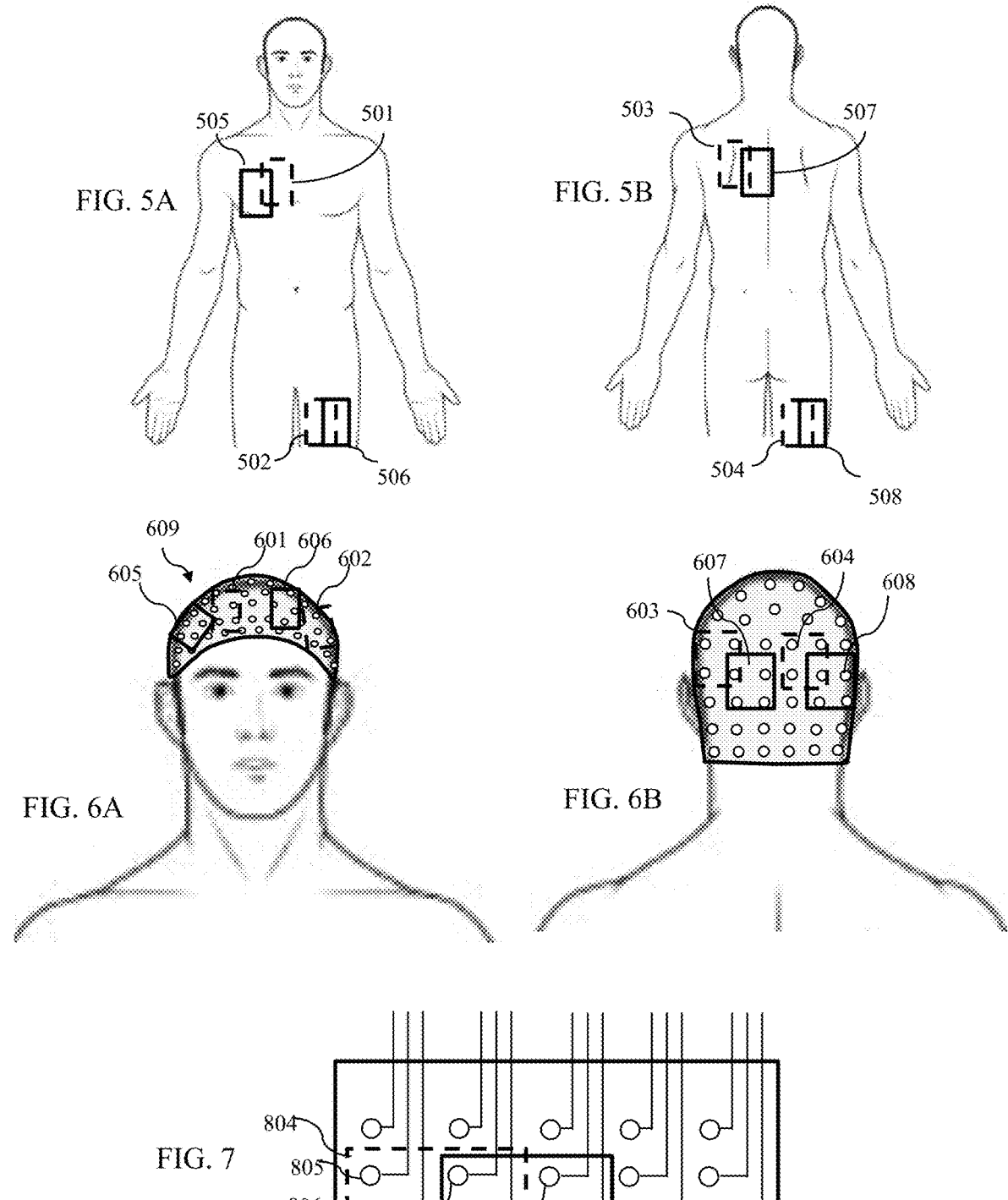

FIGS. 5A-6B depict examples of determining locations of transducers based on the region of interest for two pairs of transducers to be located. The selection of locations may be based on a plurality of regions of interest associated with a plurality of postures. In FIGS. 5A and 5B, a plurality of locations is selected on a torso of the subject's body. First, second, third, and fourth locations 501, 502, 503, and 504 are selected to locate transducers when the subject is lying on the left side, and fifth, sixth, seventh, and eighth locations 505, 506, 507, and 508 are selected to locate transducers when the subject is standing. Locations 501 and 504 may form a first pair of locations for a first pair of transducers, and locations 502 and 503 may form a second pair of locations for a second pair of transducers. Locations 505 and 508 may form the first pair of locations to locate the first pair (or a third pair) of transducers, and locations 506 and 507 may form the second pair of locations to locate the second pair (or a fourth pair) of transducers.

In FIGS. 6A and 6B, a plurality of electrode elements is integrated in one transducer array 609. The transducer array may be integrated into a helmet or a garment (e.g., hat, shirt, or pants). Multiple pairs of transducers may be selected in the transducer array 609, each transducer having a plurality of electrode elements selected from the transducer array 609. First, second, third, and fourth transducers 601, 602, 603, and 604 are selected in the transducer array 609 when the subject is lying on the left side, and fifth, sixth, seventh, and eighth transducers 605, 606, 607, and 608 are selected when the subject is standing. Transducers 601 and 603 (or transducers 605 and 607) may form the first pair of transducers, and transducers 602 and 604 (or transducers 606 and 608) may form the second pair of transducers.

FIG. 7 depicts an example transducer with individually selectable electrodes. A first set of electrode elements 804 may be selected based on the region of interest, and a second set of electrode elements 809 may be selected based on a change in the region of interest. The first set 804 includes electrode elements 805, 806, 807, and 808, and the second set 809 includes electrode elements 807, 808, 810, and 811. Electrode elements 807 and 808 are in both sets.

Figure 8:
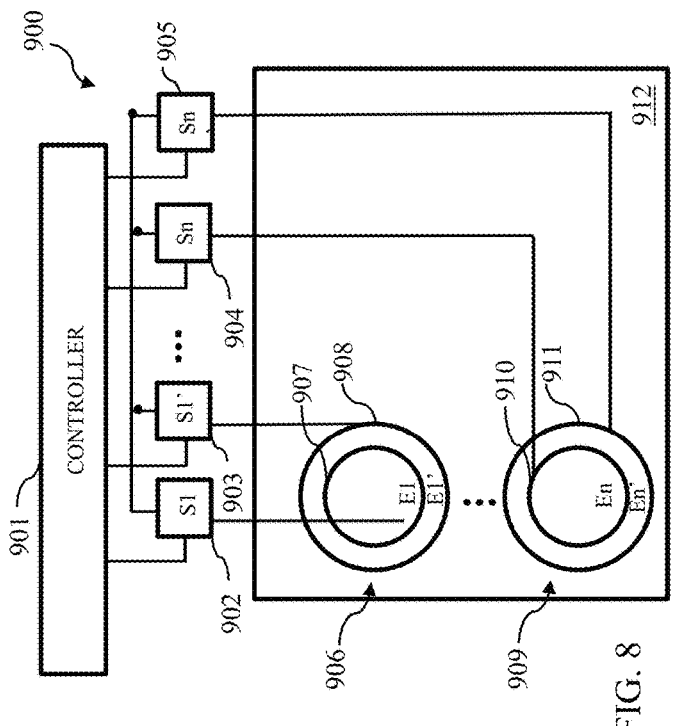

FIG. 8 depicts an example configuration of a transducer. In this example, the transducer 912 includes n electrodes, e.g., 906 and 909, and the electrodes 906 and 909 are wired to switches 902/903/904/905 controlled by a controller 901. Each electrode includes two electrode elements. Electrode 906 includes electrode elements 907 and 908 and electrode 909 includes electrode elements 910 and 911. A controller 901 may selectively turn off some switches connected to the electrodes to change the voltage signal applied to the electrodes 906 and 909 and/or to change a capacitance of the electrodes 906 and 909. Examples of the transducer are described in U.S. Patent Application Publication No. 2020/0155835 A1.

Figure 9:
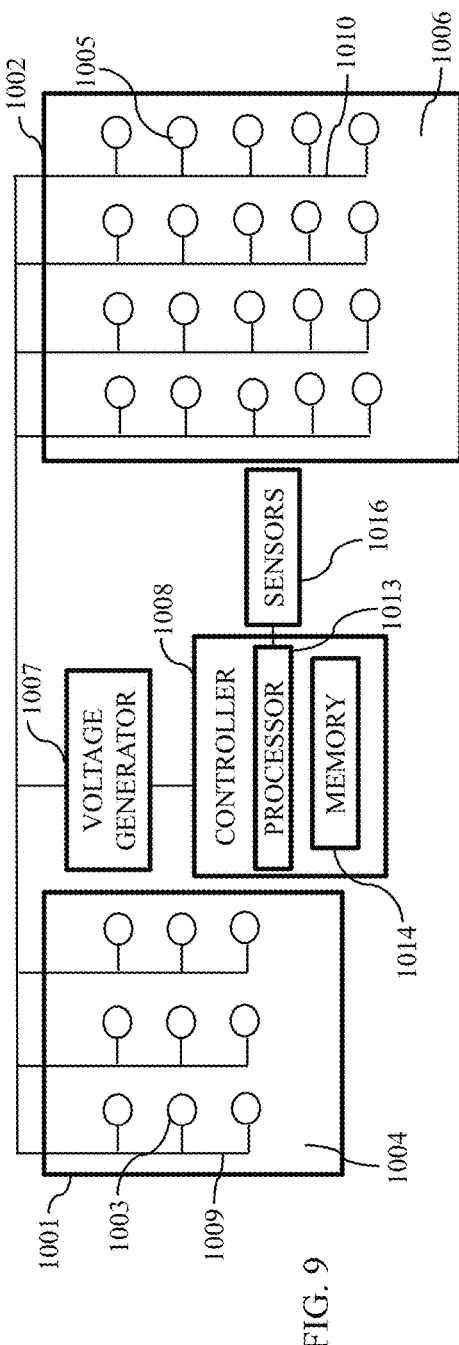
FIG. 9 depicts an example of a configuration of a pair of transducers.

FIG. 9 depicts an example configuration of a pair of transducers 1001 and 1002. Both transducers 1001/1002 may include electrode elements 1003/1005 positioned on a substrate 1004/1006 and electrically and mechanically connected through conductive wiring 1009/1010. The substrate(s) 1004/1006 may include cloth, foam, flexible plastic, and/or conductive medical gel. In another example, one or more transducers may include electrode elements that are electrically and mechanically connected without a substrate.

Transducers may be affixed to the subject's body or attached/incorporated in garment(s) covering the subject's body.

The transducers 1001 and 1002 may be connected to an AC voltage generator 1007 and a controller 1008, which may include a computer having one or more processors 1013 and memory 1014. The memory 1014 may store instructions that when executed by the one or more processors control the AC voltage generator 1007 to induce an electric field between the transducers 1001 and 1002 and/or cause the computer to perform one or more methods disclosed herein. The controller 1008 may monitor operations performed by the voltage generator 1007 and store current/voltage values in memory 1014. Other types of information (e.g., temperature values, posture information, vital signs, etc.) may be collected as well (e.g., via sensors 1016). Various types of information may be stored in a log file, which may be in the memory 1014.

Figure 10:
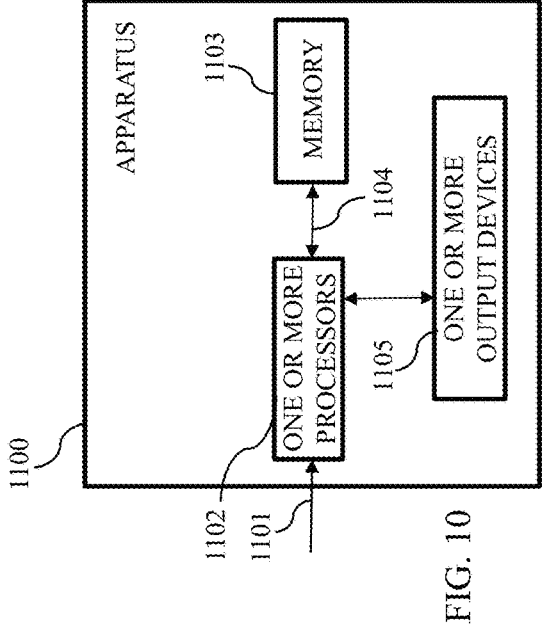
FIG. 10 depicts an example of an apparatus to determine the locations of transducers.

FIG. 10 depicts an exemplary apparatus 1100 to determine locations of transducers for applying TTFields according to various embodiments herein. The apparatus 1100 may include one or more processors 1102, a memory 1103, and one or more output devices 1105. The apparatus 1100 may be a computer. The apparatus 1100 may be incorporated into, or separate from and communicatively coupled to, the controller 1008 of FIG. 9. The memory 1103 is accessible by the one or more processors 1102, and the memory 1103 may store instructions that, when executed by the processor(s) 1102, cause the apparatus 1100 to perform one or more methods disclosed herein. Based on one or more inputs 1101, the processor(s) 1102 may generate and/or rank a plurality of locations for the transducers, and output one or more location recommendations to a user on the output device(s) 1105, or output an alert. The one or more inputs 1101 may include image data, current and voltage measurements, posture information, vital signs, physiological information, and/or user inputs.

Figure 11:
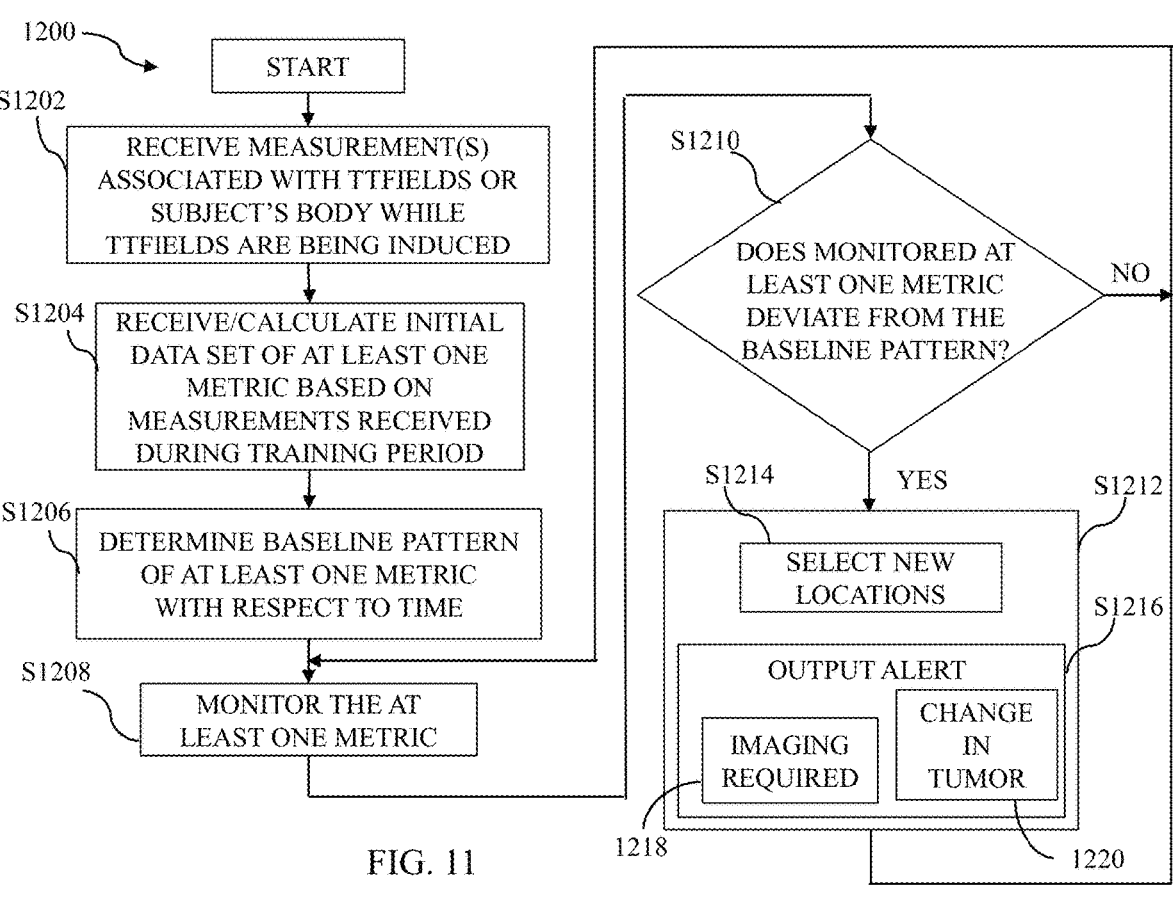
FIG. 11 depicts an example of detecting change in a subject's body.

FIG. 11 is a flowchart describing an example computer-implemented method 1200 of detecting and responding to a change in a subject's body while or after TTFields are induced in the subject's body. At step S1202, the method 1200 includes receiving one or more measurements. These may include measurement(s) associated with one or more TTFields induced in the subject's body. For example, the step S1202 may comprise receiving current and voltage measurements associated with one or more TTFields induced between at least part of a first transducer located at a first location of the subject's body and at least part of a second transducer located at a second location of the subject's body. The one or more measurements may include measurement(s) associated with the subject's body while the one or more TTFields are induced in the subject's body. For example, the measurement(s) may comprise a temperature associated with the subject's body while TTFields are induced in the subject's body. Other measurements may include those used to determine posture or vital signs of the subject's body.

The measurements received at step S1202 may be collected in real-time or near real-time while TTFields are applied. In one example, the AC generator monitors a current and voltage of the AC voltage applied to the pair of transducers and records the current and voltage measurements, for example, in a log file. In another example, one or more sensors separate from the AC generator are used to detect the current and voltage of the TTFields and generate current and voltage measurements for recording in a log file.

Multiple voltage, current, temperature, and/or other measurements may be collected during a treatment session of inducing TTFields in the subject's body. For example, voltage, current, temperature, and/or other measurements may be obtained at regular intervals (e.g., every second, five seconds, thirty seconds, minute, five minutes, ten minutes, thirty minutes, hour, two hours, four hours, or some other interval) throughout TTFields treatments.

At step S1204, the method 1200 may include receiving an initial data set of at least one metric with respect to time. The at least one metric includes a measurement associated with one or more tumor treating fields induced in the subject's body or associated with the subject's body while one or more tumor treating fields are induced in the subject's body. The initial data set may be a collection of measurement values for at least one metric stored with a time stamp.

In the initial data set, the at least one metric may comprise one or more measurements selected from the group consisting of: a resistivity associated with one or more TTFields induced in the subject's body, a current associated with one or more TTFields induced in the subject's body, a voltage associated with one or more TTFields induced in the subject's body, a differential resistivity between alternating TTFields induced in the subject's body between two pairs of transducer arrays, a sum of resistivities between alternating TTFields induced in the subject's body between two pairs of transducer arrays, an impedance associated with one or more tumor treating fields induced in the subject's body, and a temperature of the subject's body. Other metrics may be received in other embodiments.

Step S1204 may include calculating values of at least one metric (e.g., resistivity, differential resistivity, or resistivity sum) from measurements that were collected or received at step S1202 and associated with corresponding time values. For example, the step S1204 may comprise calculating a resistivity of the subject's body along a path of a TTField between at least part of the first transducer and at least part of the second transducer based on current and voltage measurements received at step S1202 according to Equation 1. As another example, the step S1204 may comprise calculating an impedance associated with one or more TTFields induced in the subject's body, using the calculation techniques discussed above.

Step S1204 may comprise calculating a set of differential resistivities with respect to time from measurements that were collected or received at step S1202. The differential resistivity metric may be a difference between a first resistivity associated with a first TTField induced between at least part of a first pair of transducer arrays at a first pair of locations of the subject's body and a second resistivity associated with a second TTField induced between at least part of a second pair of transducer arrays at a second pair of locations of the subject's body. Calculating a differential resistivity may comprise calculating an absolute value of a difference between first and second calculated resistivities for each time in the initial data set.

Step S1204 may comprise calculating a set of resistivity sums, which involves calculating a sum of first and second calculated resistivities for each time in the initial data set.

At step S1206, the method 1200 comprises determining a baseline pattern of the at least one metric with respect to time based on the initial data set. The initial data set is indicative of the at least one metric collected during a training period. The term "collected" may refer to the metric(s) either measured (e.g., via sensors) or calculated based on measurements. The "training period" may refer to a period of time during which the at least one metric is collected.

The baseline pattern may comprise a signature in the initial data set that is specific to the subject, representing a cycle related to the subject's unique physiology. The baseline pattern may capture time-dependent changes in the subject's body, such as physiological changes (e.g., sweating, hair growth, etc.), changes based on circadian rhythm (e.g., temperature, hormonal, or other changes in a 24 hour cycle), and/or changes in the subject's activities, postures, habits, vital signs, and/or locations (e.g., sleeping, sports, walking, exercising, or sitting at a desk).

The baseline pattern may be a range of values of the at least one metric averaged over a time window or the rate of change of the at least one metric averaged over the time window. For example, a time window average of one or more metrics (e.g., calculated impedance), or of the rate of change of one or more metrics, may be calculated and monitored via comparison of the value of the metric to one or more thresholds. Changes in these time window averages may be correlated with changes in the size of the tumor (FIGS. 17A-17F).

In step S1206, determining the baseline pattern may comprise applying one or more numerical analyses to the initial data set, such as performing a principal component analysis (PCA) on the initial data set. PCA involves decomposing a data set into "principal components" and using the principal components to change the basis on the data, sometimes using only a subset of more significant principal components and ignoring others. Principal components may be computed directly by a computer using the initial data set. The PCA may result in a baseline pattern comprising one or more eigenvectors and their associated eigenvalues, represented by the following equation:

$$S(t)=a_1 \cdot v_1(t)+a_2 \cdot v_2(t)+a_3 \cdot v_3(t)+ \ldots \qquad \text{Equation 4}$$

Where S(t) is the baseline pattern with respect to time; $v_1(t)$, $v_2(t)$, and $v_3(t)$ are eigenvectors representing the principal components determined for the initial data set; and $a_1$, $a_2$, and $a_3$ are eigenvalues representing amplitudes for their associated eigenvectors. Each eigenvector $v_n(t)$ may be related to physiological conditions in the subject's body, while the corresponding eigenvalue $a_n$ may be related to the strength or impact of that physiological condition on the data.

At step S1208, the method comprises monitoring the at least one metric with respect to time following the training period (e.g., during later TTFields treatment). The training period may be a period of multiple days during which one or more TTFields treatments are performed on the subject's body. Monitoring the at least one metric may involve receiving and/or calculating the at least one metric, similar to step S1204. At step S1208, monitoring the at least one metric with respect to time may be performed in real-time or near real-time during a time period in which TTFields are induced in the subject's body. Monitoring the at least one metric associated with the TTFields or the subject's body after the training period may include receiving or accessing a log file, which may occur after application of a TTFields treatment is complete. At step S1210, the method may comprise determining whether the monitored at least one metric (e.g., in new data sets) deviates from the predetermined baseline pattern.

At step S1212, the method 1200 includes triggering an event in response to detecting (at step S1210) a deviation of the monitored at least one metric from the baseline pattern.

As an example, at step S1214, the triggered event may include selecting a recommendation for adjusting location(s) of the subject's body for placement of one or more transducers based on the detected deviation. This may involve one or more of the methods discussed above with reference to FIGS. 1-4. In another example, at step S1216, the triggered event may include outputting an alert. At step S1216, outputting the alert may include outputting an alert 1218 indicating that additional imaging of the subject's body is needed. In this way, the method 1200 may serve to trigger additional imaging as needed in response to physiological changes that could represent a change in the tumor or region of interest in the subject's body. At step S1216, outputting the alert may include outputting an alert 1220 indicating a change in a tumor of the subject's body.

The process may repeat steps S1208 and S1210 until the monitored metric(s) deviate from the baseline pattern triggering an event at S1212. The process of method 1200 may begin again from step S1202 to determine a new baseline pattern based on at least one metric collected and/or calculated during a new training period, 1) if additional imaging performed on the subject indicates no change in the tumor, or 2) if transducer pairs are positioned at new locations.

FIG. 12 is a flowchart describing an example computer-implemented method 1300 of tracking physiological changes of a subject's body by detecting a deviation of a monitored metric from a baseline. FIG. 12 is an example process of performing steps S1206, S1208, and S1210 of FIG. 11. Steps S1206 and S1208 in FIG. 11 may comprise steps S1302 and S1304 of FIG. 12, respectively. Step S1210 of FIG. 11 may comprise steps S1306, S1308, and/or S1310 of FIG. 12.

At step S1302, the initial data set received at step S104 of FIG. 1 is decomposed using PCA. At step S1304, the method 1300 may include collecting one or more additional data sets of the at least one metric with respect to time. At step S1306, the method 1300 may include decomposing the one or more additional data sets of the at least one metric using, for example, the same PCA decomposition that was used on the initial data set or an altered PCA. At step S1308, the method 1300 may include comparing the one or more additional data sets to the PCA decomposition of the initial data of S1302. At step S1310, the method 1300 may include detecting a deviation of one or more additional data sets from the baseline pattern.

In an example, the comparison at S1308 may involve comparing a decomposition (S1306) of the one or more additional data sets to the PCA decomposition (S1302) of the initial data set. For example, the method 1300 may comprise decomposing at S1306 a second data set using PCA to generate a second set of eigenvectors and a second set of eigenvalues, as follows:

$$S'(t)=a'_1 \cdot v'_1(t)+a'_2 \cdot v'_2(t)+a'_3 \cdot v'_3(t)+ \ldots \qquad \text{Equation 5}$$

Where S'(t) is the PCA decomposition of the second data set with respect to time; $v'_1(t)$, $v'_2(t)$, and $v'_3(t)$ are eigenvectors representing the principal components determined for the second data set; and $a'_1$, $a'_2$, and $a'_3$ are eigenvalues representing amplitudes for the associated eigenvectors.

Using the above PCA decomposition, the comparison at S1308 may comprise comparing eigenvectors extracted from the second data set to those extracted from the initial data set (e.g., comparing $v_i(t)$ to $v'_i(t)$). At step S1310, the method 1300 may comprise detecting a deviation of the second data set from the baseline pattern in response to detecting a new eigenvector $v'_i(t)$ (1312) that is not present in the PCA decomposition of the initial data set. For example, the PCA decomposition (baseline pattern) of the initial data set may output a set of three eigenvectors $v_1(t)$, $v_2(t)$, and $v_3(t)$, while the PCA decomposition of the second data set may output a set of four eigenvectors $v'_1(t)$, $v'_2(t)$, $v'_3(t)$, and $v'_4(t)$. The number of eigenvectors (or principal components) extracted from each decomposition may be determined based on the relative impact of each principal component determined by the PCA software. In another example, the step S1306 may comprise decomposing one or more additional data sets via PCA into the same eigenvectors $v_1(t)$, $v_2(t)$, and $v_3(t)$ that were extracted from the PCA (S1302) of the initial data set. In either case, the computer may detect an emergence of a new eigenvector during the decomposition. If an eigenvector emerges after a certain time without a corresponding change in the subject's habits, this may indicate a change at the tumor level.

In another example, the step S1306 may comprise decomposing a second data set into a second set of eigenvalues corresponding to the same set of eigenvectors extracted from the PCA of the initial data set. This PCA decomposition of the second data set may be represented by the following equation:

$$S'(t)=a'_1 \cdot v_1(t)+a'_2 \cdot v_2(t)+a'_3 \cdot v_3(t)+ \ldots \text{ Equation 6}$$

Where S'(t) is the PCA decomposition of the second data set with respect to time; $v_1(t)$, $v_2(t)$, and $v_3(t)$ are eigenvectors representing the principal components determined for the initial data set; and $a'_1$, $a'_2$, and $a'_3$ are eigenvalues representing amplitudes for these associated eigenvectors based on the decomposition of the second data set. That is, the second data set is decomposed into the same eigenvectors that were identified during PCA of the initial data, and eigenvalues are determined for each of those eigenvectors to most closely fit the second data set. The eigenvalues extracted from the second data set may be compared (S1308) to those extracted from the initial data set (e.g., comparing $a_i$ to $a'_i$). At step S1310, the method 1300 may comprise detecting a deviation of the second data set from the baseline pattern in response to detecting an eigenvalue in the second set of eigenvalues $a'_i$ that crosses a threshold (1314) based on the first set of eigenvalues $a_i$. For example, the PCA decomposition of the second data set may output one or more eigenvalues $a'_1$, $a'_2$, and $a'_3$ that differ from the corresponding eigenvalues ($a_1$, $a_2$, and $a_3$) for the initial data set by a certain threshold amount or by a certain threshold percentage.

Using the decomposition of Equation 4, the comparison at S1308 may comprise comparing multiple sets of eigenvalues extracted via PCA of multiple sequential data sets to each other and to the eigenvalues extracted from the initial data set. For example, at steps S1304 and S1306, the method 1300 may comprise collecting multiple data sets of the at least one metric over time and decomposing each of the multiple data sets into another set of eigenvalues corresponding to the same set of eigenvectors extracted from the PCA of the initial data set. At step S1310, the method 1300 may comprise detecting a deviation of the multiple data sets from the baseline pattern in response to detecting a trend (1316) in the generated eigenvalue $a'_i$ of the multiple data sets corresponding to the same eigenvector of the initial data set.

In another example, the comparison at S1308 may involve comparing a signal representing the monitored at least one metric with respect to time to the PCA decomposition (S1302) of the initial data set. For example, the comparison at S1308 may include generating an initial signal representative of at least one metric with respect to time based on the first set of eigenvectors and first set of eigenvalues from the PCA of the initial data set (S1302), and then calculating a difference between this "initial signal" and the corresponding signal of the monitored at least one metric. The "initial signal" may be generated by solving a system of equations using the PCA decomposition of the initial data set (1302) to estimate a signal (the "initial signal") of a metric M taken with respect to time t for the additional data set. At step S1310, the method 1300 may comprise detecting a deviation in response to detecting that the difference between the initial signal and the corresponding signal of the metric exceeds a threshold (1318).

The decomposition of additional data sets and comparison of the data sets to the initial data set may be carried out sequentially for each new data set in real-time or near real-time during TTFields treatments. If no deviation is detected at S1310, then steps S1304-S1308 repeat.

Figure 13:
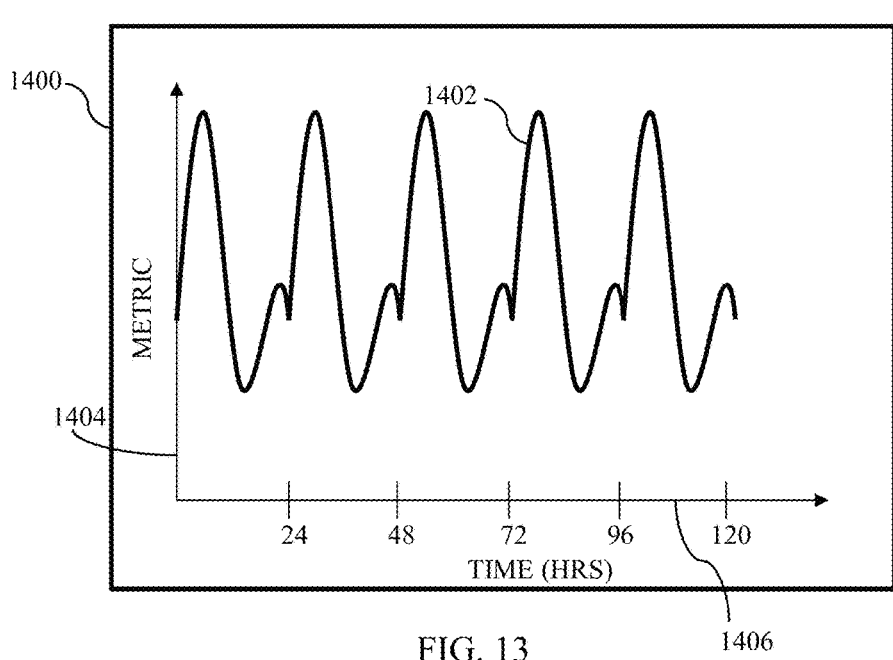
FIG. 13 depicts an example baseline pattern of a metric with respect to time.
Figure 17A:
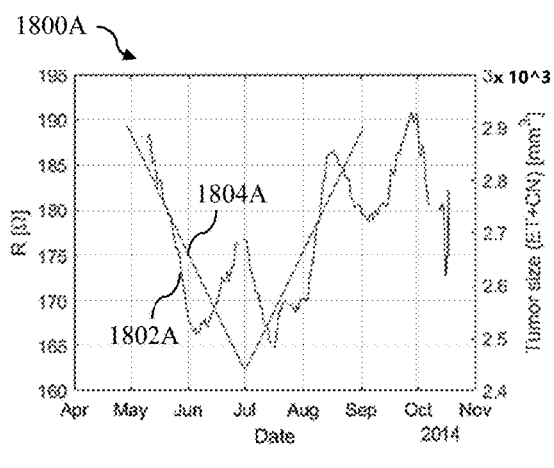
FIGS. 17A-17F depict examples of correlations between impedance and tumor size.
Figure 17B:
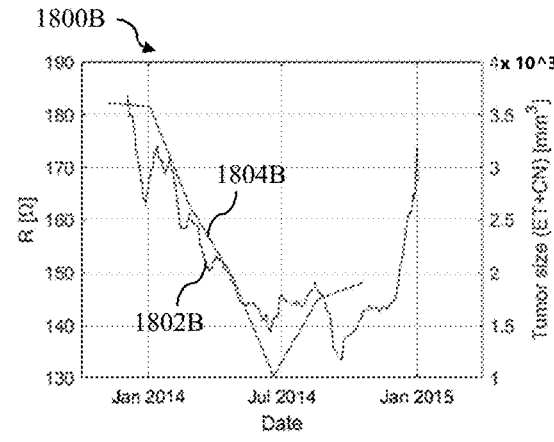
Figure 17C:
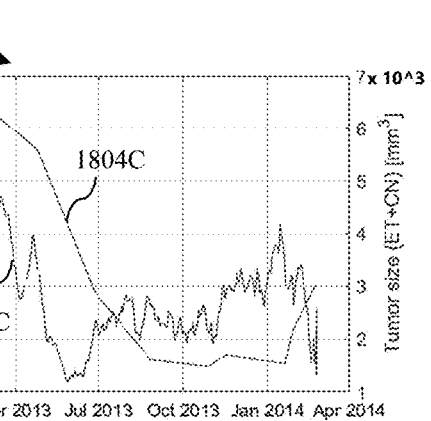
Figure 17D:
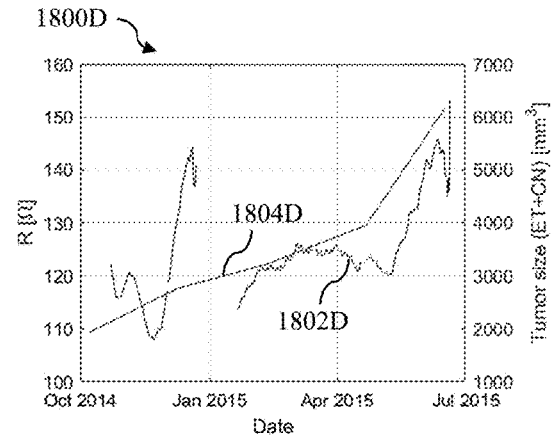
Figure 17E:
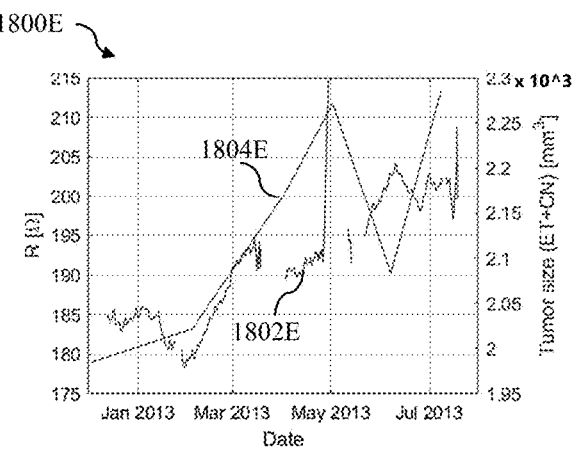
Figure 17F:
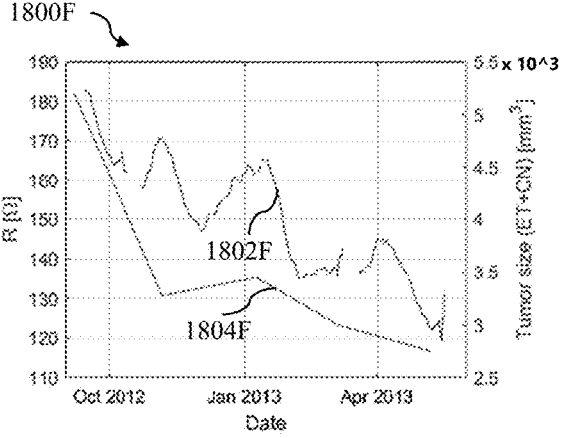

FIG. 13 depicts a plot 1400 of an example baseline pattern 1402 of a metric 1404 with respect to time 1406. As shown, the baseline pattern 1402 may represent a 24-hour cycle of the metric 1404. Although only one metric 1404 is illustrated in the plot 1400, one or more additional metrics may be monitored at the same time to determine an overall baseline pattern for the subject. The PCA of the initial data set may track a recognizable 24-hour pattern.

FIG. 14 depicts a computer-implemented method 1500 for calibrating a system for detecting changes in a subject's body while or after TTFields are induced in the subject's body, which may be performed during the training period. At step 1502, the method 1500 may include outputting a first location at which to locate a first transducer on the subject's body and a second location at which to locate a second transducer on the subject's body. The first location and second location may be output to a user interface. Step S1502 may further include outputting third and fourth locations at which to locate third and fourth transducers on the subject's body.

At step S1504, the method 1500 includes receiving one or more measurements associated with one or more TTFields induced in the subject's body or associated with the subject's body while the one or more TTFields are induced in the subject's body. In an embodiment with two pairs of transducers, receiving (S1504) the one or more measurements associated with one or more TTFields induced in the subject's body may comprise receiving one or more measurements associated with a first electric field induced between a first pair of transducers located at a first location and a second location on the subject's body and receiving one or more measurements associated with a second electric field induced between a second pair of transducers located at a third location and a fourth location on the subject's body.

At step S1506, the method 1500 includes determining an initial data set of at least one metric with respect to time based on the one or more measurements received during the training period, as discussed above. At step S1508, the method 1500 includes performing a PCA on the initial data set to generate a first set of eigenvectors and a first set of eigenvalues. At step S1510, the method 1500 includes determining a baseline pattern of the at least one metric with respect to time, the baseline pattern comprising at least a portion of the first set of eigenvectors and the first set of eigenvalues. In an example, the baseline pattern may include a subset of the total number of eigenvectors in the first set of eigenvectors and a corresponding subset of the first set of eigenvalues generated via PCA. At step 1512, the method 1500 includes storing the baseline pattern in a memory.

FIG. 15 depicts an example method 1600 for correcting for differences in transducer positioning during the process of FIG. 14, as the transducers may be removed and replaced on the subject's body periodically. At step S1602, the method 1600 includes outputting a first location to locate a first transducer on the subject's body and a second location to locate a second transducer on the subject's body. At step S1604, the method 1600 may include receiving input (e.g., image or video data) corresponding to an actual location of the first transducer on the subject's body and an actual location of the second transducer on the subject's body. At step S1606, the method 1600 may include comparing the actual location of the first transducer with the first location at which the transducer is to be placed, and comparing the actual location of the second transducer with the second location at which the transducer is to be placed.

At step S1608, the method 1600 may include correcting for any difference detected between the actual positioning of transducers and the desired first and second locations. In an example, the correction at S1608 may involve adjusting (1610) one or more measurements (e.g., those received at S1504) to correct for at least one of: a difference in positioning between the actual location of the first transducer and the first location, or a difference in positioning between the actual location of the second transducer and the second location. In another example, the correction at S1608 may involve outputting, to a user interface, instructions for correcting a positioning (1612) of at least one of the first transducer or the second transducer.

FIG. 16 depicts an example computer-implemented method to detect a change in a subject's body while or after TTFields are induced. The method 1700 includes, at step S1702, receiving current and voltage measurements associated with a first electric field induced in the subject's body, the first electric field passing through a tumor in the subject's body. The method 1700 includes, at step S1704, receiving current and voltage measurements associated with a second electric field induced in the subject's body, the second electric field passing through the tumor in the subject's body. The method 1700 includes, at step S1706, calculating a differential resistivity calculated based on the received current and voltage measurements associated with the first and second electric fields. The differential resistivity includes a difference between a first resistivity of the subject's body along a path of the first electric field and a second resistivity of the subject's body along a path of the second electric field.

The method 1700 includes, at step S1708, determining an initial data set of at least one metric with respect to time, the at least one metric including at least the differential resistivity of S1706. The initial data set is determined based on measurements collected during a training period. The method 1700 includes, at step S1710, determining a baseline pattern of the at least one metric with respect to time based on the initial data set of S1708.

The method 1700 includes, at step S1712, determining one or more additional data sets of the at least one metric with respect to time based on measurements collected following the training period. The method 1700 may include, at step S1714, determining whether the at least one metric associated with the one or more additional data sets deviates from the baseline pattern of S1710. If no deviation is detected, the method 1700 proceeds back to S1712. If a deviation of the additional data sets from the baseline pattern is detected, the method 1700 proceeds to step S1716, which includes outputting an alert in response to detecting a deviation of the at least one metric in the one or more additional data sets from the baseline pattern. Step S1716 may include outputting an indication 1718 that additional imaging of the subject's body is needed, outputting an indication 1720 of a change in a tumor of the subject's body, or a combination thereof.

FIGS. 17A-17F depict examples of relationships between calculated impedance measurements taken throughout TTFields treatment and tumor size determined via image data. Each of FIGS. 17A-17F provides a plot 1800 (i.e., 1800A, 1800B, 1800C, 1800D, 1800E, and 1800F) showing trend lines of calculated impedance 1802 (i.e., 1802A, 1802B, 1802C, 1802D, 1802E, and 1802F) with respect to time and of a determined tumor size 1804 (i.e., 1804A, 1804B, 1804C, 1804D, 1804E, and 1804F) with respect to time. Each plot 1800 corresponds to actual measurements/ determinations made for one of six patients during clinical trials. The impedance 1802 is a sum total of the impedance between two channels delivering TTFields (e.g., a first channel between a first pair of transducers and a second channel between a second pair of transducers). The tumor size 1804 is an estimation of tumor volume calculated based on MRI images from the patients. The trend line for tumor size 1804 is shown via straight lines connecting multiple tumor size values at different times (corresponding to MRIs taken at distinct points during TTFields treatment). The trend line for impedance 1802 provides average impedance values taken via window averaging of the impedance over a period of 15 days. The measurement shown for each day is an average of impedance values at the current day, the prior 7 days, and the following 7 days. Times where no impedance values are shown correspond to times in which the transducers were not used or there was no access to the log files.

As illustrated in FIGS. 17A-17F, the calculated impedance 1802 is correlated to the determined tumor size 1804. Thus, impedance measurements can be used to track tumor progression. Changes in impedance values may be used to track changes in the region of interest (e.g., tumor) over time without needing to take an MRI. Calculating and tracking the impedance may be used to 1) determine when a next MRI should be taken, 2) select new pairs of locations for placement of transducers, or both. For example, current and voltage measurements associated with tumor treating fields induced in the subject's body may be received and then used to calculate an impedance associated with the subject's body; the impedance may be monitored with respect to time while TTFields are induced in the subject's body; and upon detecting a deviation of the monitored impedance from a baseline (e.g., impedance values and/or rate of change thereof), an event may be triggered.

The invention includes other illustrative embodiments ("Embodiments") as follows.

Embodiment 1: A method of applying tumor treating fields to a region of interest of a subject's body corresponding to a tumor of the subject's body, comprising: alternately applying to the region of interest a first electric field between a first pair of locations of the subject's body and a second electric field between a second pair of locations of the subject's body; detecting a change in the region of interest of the subject's body; ceasing applying the first electric field and the second electric field; selecting, based on the detected change in the region of interest, a third pair of locations of the subject's body and a fourth pair of locations of the subject's body, the third and fourth pairs of locations being different than the first and second pairs of locations; and alternately applying to the region of interest a third electric field between the third pair of locations of the subject's body and a fourth electric field between the fourth pair of locations of the subject's body.

Embodiment 1 may be combined with features of any of Embodiments 2-7, taken alone or in combination with each other. Embodiment 2: the change in the region of interest is determined based on a posture change of the subject's body, and the posture change of the subject's body comprises a change from one of a plurality of postures to another of the plurality of postures, the plurality of postures comprises at least two of standing, sitting, lying down, or one or more postures in-between standing, sitting, and lying down. Embodiment 3: the lying down posture comprises the subject lying on at least one of the subject's back, left side, right side, or chest. Embodiment 4: the change in the region of interest is determined based on a posture change of the subject's body, the posture change is detected by one or more sensors. Embodiment 5: the one or more sensors to detect the posture change are located external to the first pair of transducers and the second pair of transducers. Embodiment 6: the one or more sensors to detect the posture change are part of at least one of the first pair of transducers or the second pair of transducers. Embodiment 7: the region of interest is determined by image data of the subject's body, a voltage measurement and a current measurement of an applied electric field, or a combination thereof.

Embodiment 8: A method of applying tumor treating fields to a region of interest of a subject's body corresponding to a tumor of the subject's body, the method using a first pair of transducers and a second pair of transducers, comprising: alternately applying to the region of interest a first electric field between a first part of the first pair of transducers and a second electric field between a first part of the second pair of transducers; determining a change in the region of interest of the subject's body; ceasing applying the first electric field and the second electric field; selecting, based on the change in the region of interest, a second part of the first pair of transducers and a second part of the second pair of transducers; and alternately applying to the region of interest a third electric field between the second part of the first pair of transducers and a fourth electric field between the second part of the second pair of transducers.

Embodiment 8 may be combined with features of any of Embodiments 9-11, taken alone or in combination. Embodiment 9: the first part of the two pairs of transducers do not overlap with one another, and the second part of the two pairs of transducers do not overlap with one another. Embodiment 10: the first part of the two pairs of transducers at least partially overlap with one another, and the second part of the two pairs of transducers at least partially overlap with one another. Embodiment 11: a first angle between a first line defined by the first part of the first pair of transducers and a second line defined by the first part of the second pair of transducers is approximately 90 degrees+/−20 degrees; and a second angle between a third line defined by the second part of the first pair of transducers and a fourth line defined by the second part of the second pair of transducers is approximately 90 degrees+/−20 degrees.

Embodiment 12: A method of applying tumor treating fields to a region of interest of a subject's body corresponding to a tumor of the subject's body, comprising: alternately inducing a first electric field between a first pair of transducers located at a first pair of locations of the subject's body and a second electric field between a second pair of transducers located at a second pair of locations of the subject's body; determining a change in the region of interest of the subject's body; ceasing the first and second electric fields; selecting, based on the change in the region of interest, a third pair of locations of the subject's body and a fourth pair of locations of the subject's body; the third and fourth pairs of locations being different than the first and second pairs of locations; and either: alternately inducing a third electric field between the first pair of transducers located at the third pair of locations of the subject's body and a fourth electric field between the second pair of transducers located at the fourth pair of locations of the subject's body, or alternately inducing a third electric field between a third pair of transducers located at the third pair of locations of the subject's body and a fourth electric field between a fourth pair of transducers located at the fourth pair of locations of the subject's body.

Embodiment 13: The method of Embodiment 12, wherein the change in the region of interest is caused by a change in at least one of a location of the tumor or a size of the tumor.

Embodiment 14: A computer-implemented method for determining locations of transducers on a subject's body for applying tumor treating fields to a tumor of the subject's body, comprising: determining a plurality of postures of the subject's body; determining, for each posture, a corresponding region of interest of the subject's body corresponding to the tumor; selecting a plurality of pairs of locations on the subject's body, each pair of locations having a first location to locate a first transducer and a second location to locate a second transducer; and selecting and outputting, for each posture, one or more recommended pairs of locations based on the corresponding region of interest for each the plurality of postures of the subject's body.

Embodiment 15: A method of applying tumor treating fields to a tumor of a subject's body using a plurality of electrode elements, comprising: determining a plurality of postures of the subject's body; selecting, for each posture, a plurality of pairs of electrode element arrays, each electrode element array including one or more electrode elements; inducing, for each posture, an electric field between each of the corresponding pair of electrode element arrays for the posture, the induced electric field passing through the tumor; obtaining, for each posture, a voltage measurement and a current measurement for each induced electric field between each pair of electrode element arrays; calculating, for each posture, a field density or a resistivity based on the voltage measurement and the current measurement for each induced electric field between each pair of electrode element arrays; and selecting and outputting, for each posture, one or more recommended pairs of arrays of electrode elements based on the calculated field density or the calculated resistivity.

Embodiment 16: A system to apply tumor treating fields to a subject's body, comprising: a plurality of transducers adapted to be located at a plurality of pairs of locations on the subject's body, each pair of locations having a first location to place a first transducer on the subject's body and a second location to place a second transducer on the subject's body; a voltage generator adapted be coupled to at least two of the transducers and capable of inducing an electric field to treat a tumor in the subject's body using the coupled transducers; one or more sensors adapted to detect posture information of the subject's body; a controller coupled to the voltage generator and the one or more sensors, the controller comprising one or more processors and a memory accessible by the one or more processors, the memory storing instructions that when executed by the one or more processors, cause the controller to: determine a posture from a plurality of postures based on the posture information from the one or more sensors; select a pair of locations among the plurality of pairs of locations based on the determined posture, and instruct the voltage generator to generate voltages to induce electric fields between the first transducer and the second transducer of the selected pair of locations to treat the tumor in the subject's body.

Embodiment 17: An apparatus for determining locations of transducers on a subject's body for applying tumor treating fields, comprising: one or more sensors; one or more processors; and memory accessible by the one or more processors, the memory storing instructions that when executed by the one or more processors, cause the apparatus to: receive location information corresponding to a plurality of pairs of locations on the subject's body, each pair of locations having one first location to locate a first transducer and one second location to locate a second transducer; receive posture information corresponding to each of a plurality of postures of the subject's body from the one or more sensors; receive, for each posture, tumor treating fields information for respective location information for a corresponding pair of locations; and select and output, for each posture, one or more recommend pairs of locations based on the tumor treating fields information.

Embodiment 18: A computer-implemented method to detect and respond to a change in a subject's body while or after tumor treating fields are induced in the subject's body, comprising: receiving an initial data set of at least one metric with respect to time, the at least one metric including a measurement associated with one or more tumor treating fields induced in the subject's body or associated with the subject's body while one or more tumor treating fields are induced in the subject's body; determining a baseline pattern of the at least one metric with respect to time based on the initial data set indicative of the at least one metric collected during a training period; monitoring the at least one metric with respect to time following the training period; and triggering an event in response to detecting a deviation of the monitored at least one metric from the baseline pattern.

Embodiment 18 may be combined with features of any of Embodiments 19-28, taken alone or in combination with each other. Embodiment 19: the initial data set includes the at least one metric measured at regular intervals throughout the training period. Embodiment 20: determining the baseline pattern comprises decomposing the initial data set of the at least one metric with respect to time using principal component analysis, the baseline pattern comprises a first set of eigenvectors and a first set of eigenvalues resulting from the principal component analysis. Embodiment 21: monitoring the at least one metric with respect to time comprises: collecting a second data set of the at least one metric with respect to time; and comparing the second data set to the principal component analysis decomposition of the initial data set. Embodiment 22: decomposing the second data set using principal component analysis to generate a second set of eigenvectors and a second set of eigenvalues; and triggering the event in response to detecting a new eigenvector in the second set of eigenvectors that is different from and in addition to the eigenvectors of the first set of eigenvectors. Embodiment 23: decomposing the second data set into a second set of eigenvalues corresponding to the first set of eigenvectors; and triggering the event in response to detecting an eigenvalue in the second set of eigenvalues that crosses a threshold based on the first set of eigenvalues. Embodiment 24: collecting multiple data sets of the at least one metric over time including the second data set; decomposing each of the multiple data sets into another set of eigenvalues corresponding to the first set of eigenvectors; and triggering the event in response to detecting a trend in an eigenvalue corresponding to the same eigenvector of the first set of eigenvectors over time. Embodiment 25: monitoring the at least one metric with respect to time is performed while tumor treating fields are induced in the subject's body. Embodiment 26: receiving the initial data set comprises receiving current and voltage measurements associated with the one or more tumor treating fields induced in the subject's body; and determining the baseline pattern comprises calculating values for the at least one metric in the initial data set based on the received current and voltage measurements, the at least one metric comprises a resistivity along a path of the subject's body or a differential resistivity between two paths through the subject's body. Embodiment 27: the current and voltage measurements are recorded in a log file of a computer communicatively coupled to a device capable of determining the current and voltage measurements. Embodiment 28: the one or more tumor treating fields are induced between at least part of a first transducer and at least part of a second transducer.

Embodiment 29: A computer-implemented method to detect a change in a subject's body while or after tumor treating fields are induced in the subject's body, comprising: receiving an initial data set of at least one metric with respect to time, the at least one metric including a measurement associated with one or more tumor treating fields induced in the subject's body or associated with the subject's body while one or more tumor treating fields are induced in the subject's body; determining a baseline pattern of the at least one metric with respect to time based on the initial data set indicative of the at least one metric collected during a training period; monitoring the at least one metric with respect to time following the training period; and outputting an alert in response to detecting a deviation of the monitored at least one metric from the baseline pattern.

Embodiment 30: A computer-implemented method to calibrate a system for detecting changes in a subject's body while or after tumor treating fields are induced in the subject's body, comprising: receiving one or more measurements associated with one or more tumor treating fields induced in the subject's body or associated with the subject's body while one or more tumor treating fields are induced in the subject's body; determining an initial data set of at least one metric with respect to time based on the one or more measurements received during a training period; performing a principal component analysis on the initial data set of the at least one metric with respect to time to generate a first set of eigenvectors and a first set of eigenvalues; determining a baseline pattern of the at least one metric with respect to time, the baseline pattern comprising at least a portion of the first set of eigenvectors and the first set of eigenvalues; and storing the baseline pattern in a memory.

Embodiment 30 may be combined with features of any of Embodiments 31-36, taken alone or in combination with each other. Embodiment 31: outputting, to a user interface, a first location to locate a first transducer on the subject's body and a second location to locate a second transducer on the subject's body; the one or more received measurements are associated with a tumor treating field induced between at least part of the first transducer located at the first location of the subject's body and at least part of the second transducer located at the second location of the subject's body. Embodiment 32: receiving input corresponding to an actual location of the first transducer on the subject's body and an actual location of the second transducer on the subject's body; comparing the actual location of the first transducer with the first location; and comparing the actual location of the second transducer with the second location. Embodiment 33: adjusting the one or more measurements to correct for at least one of: a difference in positioning between the actual location of the first transducer and the first location, or a difference in positioning between the actual location of the second transducer and the second location. Embodiment 34: outputting, to a user interface, instructions for correcting a positioning of at least one of the first transducer or the second transducer in response to determining that at least one of the actual first location or the actual second location does not correspond to the first location or the second location on the subject's body. Embodiment 35: receiving the one or more measurements associated with one or more tumor treating fields induced in the subject's body comprises: receiving one or more measurements associated with a first electric field induced between a first pair of transducers located at a first location and a second location on the subject's body; and receiving one or more measurements associated with a second electric field induced between a second pair of transducers located at a third location and a fourth location on the subject's body. Embodiment 36: the baseline pattern includes a subset of the first set of eigenvectors and a corresponding subset of the first set of eigenvalues.

Embodiment 37: A computer-implemented method to detect a change in a subject's body while or after tumor treating fields are induced in the subject's body, comprising: receiving current and voltage measurements associated with a first electric field induced in the subject's body, the first electric field passing through a tumor in the subject's body; receiving current and voltage measurements associated with a second electric field induced in the subject's body, the second electric field passing through the tumor in the subject's body; calculating a differential resistivity based on the received current and voltage measurements associated with the first and second electric fields, the differential resistivity comprising a difference between a first resistivity of the subject's body along a path of the first electric field and a second resistivity of the subject's body along a path of the second electric field; determining an initial data set of at least one metric with respect to time, the at least one metric including at least the differential resistivity, wherein the initial data set is determined based on measurements collected during a training period; determining a baseline pattern of the at least one metric with respect to time based on the initial data set; determining one or more additional data sets of the at least one metric with respect to time based on measurements collected following the training period; and outputting an alert in response to detecting a deviation of the at least one metric in the one or more additional data sets from the baseline pattern.

Embodiment 38: A method of applying tumor treating fields to a region of interest of a subject's body corresponding to a tumor of the subject's body, the method using a first pair of transducers having a plurality of electrodes and a second pair of transducers having a plurality of electrodes, the method comprising: alternately applying to the region of interest a first electric field between a first set of electrodes of the first pair of transducers and a second electric field between a first set of electrodes of the second pair of transducers; determining a change in the region of interest of the subject's body; ceasing applying the first electric field and the second electric field; selecting, based on the change in the region of interest, a second set of electrodes of the first pair of transducers and a second set of electrodes of the second pair of transducers; and alternately applying to the region of interest a third electric field between the second set of electrodes of the first pair of transducers and a fourth electric field between the second set of electrodes of the second pair of transducers.

Embodiment 38 may be combined with features of any of Embodiments 39-49, taken alone or in combination with each other. Embodiment 39: a first electrode is in both the first and second sets of electrodes of the first pair of transducers, the first electrode emits energy during the first electric field and during the third electric field, and the energy emitted by the first electrode during the first electric field is different than the energy emitted by the first electrode during the third electric field. Embodiment 40: the energy emitted by the first electrode during the first electric field is a percentage of the energy emitted by the first electrode during the third electric field, the percentage being greater than 0% and less than 100%, or the energy emitted by the first electrode during the third electric field is a percentage of the energy emitted by the first electrode during the first electric field, the percentage being greater than 0% and less than 100%. Embodiment 41: the first electrode has a first capacitance during the first electric field and a second capacitance different from the first capacitance during the third electric field. Embodiment 42: the first electrode receives a same voltage signal during the first and third electric fields but has different capacitances during the first and third electric fields. Embodiment 43: the first electrode receives different voltages for the first and third electric fields. Embodiment 44: the first electrode receives a first non-zero voltage during the first electric field and a second non-zero voltage different from the first non-zero voltage during the third electric field. Embodiment 45: the first electrode receives a same amplitude of voltage during the first and third electric fields but during different time segments of periods of the first and third electric fields. Embodiment 46: the first electrode emits energy during a first portion in a period of the first electric field and during a first portion in a period of the third electric field, and the energy emitted during the first portion in the period of the first electric field is different than the energy emitted during the first portion in the period of the third electric field. Embodiment 47: the first electrode is separately controllable from the other electrodes in the first and second sets of electrodes of the first pair of transducers. Embodiment 48: the electrodes of the first and second pairs of transducers are individually addressable, at least one individually addressable electrode of the first pair of transducers emits different non-zero energy during the first and third electric fields, and at least one individually addressable electrode of the second pair emits different non-zero energy during the second and fourth electric fields. Embodiment 49: at least one electrode of the first pair of transducers emits different amounts of non-zero energy during the first and third electric fields, and at least one electrode of the second pair of transducers emits different amounts of non-zero energy during the second and fourth electric fields.

Embodiment 50: A computer-implemented method to detect and respond to a change in a subject's body while or after tumor treating fields are induced in the subject's body, comprising: receiving current and voltage measurements associated with tumor treating fields induced in the subject's body; calculating an impedance associated with the subject's body based on the current and voltage measurements; monitoring the impedance with respect to time while tumor treating fields are induced in the subject's body; and triggering an event in response to detecting a deviation of the monitored impedance from a baseline.

Embodiments illustrated under any heading or in any portion of the disclosure may be combined with embodiments illustrated under the same or any other heading or other portion of the disclosure unless otherwise indicated herein or otherwise clearly contradicted by context.

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method to detect and respond to a change in a subject's body while or after tumor treating fields are induced in the subject's body, the computer-implemented method comprising:
receiving an initial data set of at least one metric for a plurality of time intervals, the at least one metric comprising or based on:
at least one of a voltage, a current, or a resistance of an electric field of one or more tumor treating fields induced in the subject's body using at least a first pair of transducers placed on and external to the subject's body; and
a measurement associated with the subject's body while the one or more tumor treating fields are induced in the subject's body using at least the first pair of transducers placed on and external to the subject's body,
wherein the initial data set is collected during the plurality of time intervals while the one or more tumor treating fields are induced in the subject's body;
determining a baseline pattern of the at least one metric with respect to time based on the initial data set indicative of the at least one metric collected during a training period;
monitoring the at least one metric with respect to time following the training period; and
triggering an event in response to detecting a deviation of the monitored at least one metric from the baseline pattern.

2. The computer-implemented method of claim 1, wherein the at least one metric further comprises or is further based on at least one of:
a difference between a first resistivity associated with a first tumor treating field induced between at least part of the first pair of transducer arrays at a first pair of locations of the subject's body and a second resistivity associated with a second tumor treating field induced between at least part of a second pair of transducer arrays at a second pair of locations of the subject's body; or
an impedance associated with the one or more tumor treating fields induced in the subject's body.

3. The computer-implemented method of claim 1, wherein the baseline pattern represents a 24-hour cycle of the at least one metric.

4. The computer-implemented method of claim 1, wherein the baseline pattern is a range of values of the at least one metric averaged over a time window or of the rate of change of the at least one metric averaged over the time window.

5. The computer-implemented method of claim 1, wherein the training period is a period of multiple days.

6. The computer-implemented method of claim 1, wherein determining the baseline pattern comprises decomposing the initial data set of the at least one metric with respect to time using principal component analysis, wherein the baseline pattern comprises a first set of eigenvectors and a first set of eigenvalues resulting from the principal component analysis.

7. The computer-implemented method of claim 6, wherein monitoring the at least one metric with respect to time comprises:

collecting a second data set of the at least one metric with respect to time; and comparing the second data set to the principal component analysis decomposition of the initial data set.

8. The computer-implemented method of claim 6, further comprising:

generating an initial signal representative of the at least one metric with respect to time based on the first set of eigenvectors and first set of eigenvalues resulting from the principal component analysis;

calculating a difference between the initial signal and a corresponding signal of the monitored at least one metric with respect to time; and triggering the event in response to detecting the difference between the initial signal and the corresponding signal exceeds a threshold.

9. The computer-implemented method of claim 1, wherein the event comprises at least one of:

outputting an alert indicating a change in a tumor of the subject's body;

outputting an alert that additional imaging of the subject's body is needed; or selecting, based on the detected deviation, a recommendation for adjusting locations of the subject's body for placement of transducers used to generate the tumor treating fields.

10. The computer-implemented method of claim 1, wherein the plurality of time intervals are separated by regular time intervals, wherein the regular time intervals are one of one second, five seconds, thirty seconds, one minute, five minutes, ten minutes, thirty minutes, hour, two hours, or four hours.

11. The computer-implemented method of claim 1, wherein the measurement associated with the subject's body comprises at least one of:

a temperature of the subject's body while the one or more tumor treating fields are induced in the subject's body;

a posture of the subject's body while the one or more tumor treating fields are induced in the subject's body; or one or more vital signs of the subject's body the one or more while tumor treating fields are induced in the subject's body.

12. A computer-implemented method to detect and respond to a change in a subject's body while or after tumor treating fields are induced in the subject's body, the computer-implemented method comprising:

receiving an initial data set of at least one metric for a plurality of time intervals, the at least one metric comprising or based on:

at least one of a voltage, a current, or a resistance of an electric field of one or more tumor treating fields induced in the subject's body using at least a first pair of transducers placed on and external to the subject's body; and a measurement associated with the subject's body while the one or more tumor treating fields are induced in the subject's body using at least the first pair of transducers placed on and external to the subject's body, wherein the initial data set is collected during the plurality of time intervals while the one or more tumor treating fields are induced in the subject's body;

determining a baseline pattern of the at least one metric with respect to time based on the initial data set indicative of the at least one metric collected during a training period;

monitoring the at least one metric with respect to time following the training period; and triggering an event in response to detecting a deviation of the monitored at least one metric from the baseline pattern, wherein the event comprises at least one of:

outputting an alert indicating a change in a tumor of the subject's body;

outputting an alert that additional imaging of the subject's body is needed; or selecting, based on the detected deviation, a recommendation for adjusting locations of the subject's body for placement of transducers used to generate the tumor treating fields.

13. The computer-implemented method of claim 12, wherein the at least one metric further comprises or is further based on at least one of:

a difference between a first resistivity associated with a first tumor treating field induced between at least part of the first pair of transducer arrays at a first pair of locations of the subject's body and a second resistivity associated with a second tumor treating field induced between at least part of a second pair of transducer arrays at a second pair of locations of the subject's body; or an impedance associated with the one or more tumor treating fields induced in the subject's body.

14. The computer-implemented method of claim 12, wherein the baseline pattern represents a 24-hour cycle of the at least one metric.

15. The computer-implemented method of claim 12, wherein the baseline pattern is a range of values of the at least one metric averaged over a time window or of the rate of change of the at least one metric averaged over the time window.

16. The computer-implemented method of claim 12, wherein the training period is a period of multiple days.

17. The computer-implemented method of claim 12, wherein determining the baseline pattern comprises decomposing the initial data set of the at least one metric with respect to time using principal component analysis, wherein the baseline pattern comprises a first set of eigenvectors and a first set of eigenvalues resulting from the principal component analysis.

18. The computer-implemented method of claim 17, wherein monitoring the at least one metric with respect to time comprises:

collecting a second data set of the at least one metric with respect to time; and comparing the second data set to the principal component analysis decomposition of the initial data set.

19. The computer-implemented method of claim 17, further comprising:

generating an initial signal representative of the at least one metric with respect to time based on the first set of eigenvectors and first set of eigenvalues resulting from the principal component analysis;

calculating a difference between the initial signal and a corresponding signal of the monitored at least one metric with respect to time; and triggering the event in response to detecting the difference between the initial signal and the corresponding signal exceeds a threshold.

20. The computer-implemented method of claim 12, wherein the plurality of time intervals are separated by regular time intervals, wherein the regular time intervals are one of one second, five seconds, thirty seconds, one minute, five minutes, ten minutes, thirty minutes, hour, two hours, or four hours.

\* \* \* \* \*